United States Patent
Stark et al.

(10) Patent No.: US 12,158,446 B2
(45) Date of Patent: Dec. 3, 2024

(54) MEASURING SYSTEM FOR DETERMINING GAS CONCENTRATIONS

(71) Applicant: Drägerwerk AG & Co. KGaA, Lübeck (DE)

(72) Inventors: Hartmut Stark, Lübeck (DE); Günter Steinert, Lübeck (DE); Hans-Ullrich Hansmann, Lübeck (DE); Tobias Heise, Lübeck (DE); Robert Jahns, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 65 days.

(21) Appl. No.: 17/960,378

(22) Filed: Oct. 5, 2022

(65) Prior Publication Data
US 2023/0114548 A1  Apr. 13, 2023

(30) Foreign Application Priority Data
Oct. 8, 2021  (DE) .......................... 102021126106.6

(51) Int. Cl.
G01N 27/74  (2006.01)
G01N 33/00  (2006.01)

(52) U.S. Cl.
CPC ......... *G01N 27/74* (2013.01); *G01N 33/0036* (2013.01)

(58) Field of Classification Search
CPC ............... G01N 27/74; G01N 33/0036; G01N 21/3504; G01N 33/497; G01N 33/0004; G01N 27/4074; G01N 33/0027; G01N 33/00; G01N 33/0073; G01N 1/22; G01N 2291/0215; G01N 31/225; G01N 2291/0212
See application file for complete search history.

(56) References Cited

U.S. PATENT DOCUMENTS

| | | | |
|---|---|---|---|
| 2,944,418 A | 7/1960 | Engelhardt |
| 3,584,499 A | 6/1971 | Hummel |
| 3,646,803 A | 3/1972 | Meyer |
| 4,683,426 A | 7/1987 | Hummel |
| 4,808,921 A | 2/1989 | Christensen |

(Continued)

FOREIGN PATENT DOCUMENTS

DE  102006009370 A1  9/2007
EP  0157247 A2 * 10/1985 ............. G01N 27/74

*Primary Examiner* — Peter J Macchiarolo
*Assistant Examiner* — Anthony W Megna Fuentes
(74) *Attorney, Agent, or Firm* — McGlew and Tuttle, P.C.

(57) ABSTRACT

A measurement system (100) determines gas concentrations in a gas mixture of a gas sample by utilizing thermal conductivities and paramagnetic effects of thermal conductivities in the gas mixture involving data sets (203). A circuit arrangement provides measured values with an AC signal component and with a DC signal component to a calculation and control unit (200). An oxygen concentration in the gas mixture of the gas sample is determined based on the standardized AC signal components and a concentration of another gas in the gas mixture of the gas sample is determined based on the standardized DC voltage signal components. Output signals are generated by the calculation and control unit, which indicate the determined oxygen concentration and the determined concentration of another gas in the gas mixture of the gas sample.

20 Claims, 15 Drawing Sheets

(56) References Cited

U.S. PATENT DOCUMENTS

| | | |
|---|---|---|
| 6,405,578 B2 | 6/2002 | Chiba et al. |
| 6,430,987 B1 | 8/2002 | Stark |
| 6,895,802 B2 | 5/2005 | Stark et al. |
| 6,952,947 B2 | 10/2005 | Steinert et al. |
| 8,596,109 B2 | 12/2013 | Stark et al. |
| 9,360,441 B2 | 6/2016 | Heise et al. |
| 2011/0094293 A1 | 4/2011 | Klein |
| 2011/0252868 A1* | 10/2011 | Doring .................. G01N 27/74 |
| | | 73/25.02 |

* cited by examiner

MEASURING SYSTEM FOR DETERMINING GAS CONCENTRATIONS

CROSS REFERENCE TO RELATED APPLICATIONS

This application claims the benefit of priority under 35 U.S.C. § 119 of German Application 10 2021 126 106.6, filed Oct. 8, 2021, the entire contents of which are incorporated herein by reference.

TECHNICAL FIELD

The present invention relates to a measurement system for determining gas concentrations in a gas mixture. In particular, the invention relates to a device for measuring the concentrations of paramagnetic gases in a gas sample, such as the concentrations of oxygen and other gases in the respiratory gas, such as an anesthetic gas of a patient to be ventilated and/or anesthetized. According to the invention, the measuring system is capable of detecting an oxygen concentration and a concentration of at least one further gas in a gas mixture of a gas sample. Gases which are used in clinical use, in particular in the environment of anesthesia, intensive medicine, emergency medicine for supplying patients with respiratory gases, can be considered as further gases. These include, for example, nitrous oxide, anesthetic gases such as halothane, desflurane, enflurane, sevoflurane, isoflurane and xenon, as well as carbon dioxide, trace gases and argon.

BACKGROUND

Paramagnetic methods are often used to determine the oxygen concentration in gases, based on the fact that oxygen molecules are paramagnetic due to their permanent magnetic dipole moment, whereas most other gases exhibit diamagnetic properties. It is generally known that the thermal conductivity of paramagnetic gases changes under the influence of magnetic fields. The cause of this behavior is apparently the fact that paramagnetic gases possess a permanent magnetic moment, which, however, does not normally appear externally, due to the thermal molecular motion of the gas molecules. A sufficiently strong external magnetic field, however, ensures that the magnetic dipole moments of the individual molecules are aligned. On the one hand, this causes a change in the susceptibility, which results in an increase in the magnetic flux, and on the other hand, a certain molecular arrangement is established in the gas, which limits the degrees of freedom and thus the possibilities of transferring thermal energy to neighboring molecules via collisions. This changes to a small extent the thermal conductivity of the gas. Paramagnetic measuring devices for the determination of oxygen concentrations, in particular also in breathing gases, are known for example from the following U.S. Pat. No. 6,952,947 BB, US2011094293 AA, U.S. Pat. Nos. 8,596,109 BB, 9,360,441 BB, 6,895,802 BB, 6,405,578 BB, 6,430,987 BA, 4,808,921 A, 4,683,426 A, 3,646,803 A, 3,584,499 A, 2,944,418 A.

A basic principle for measuring oxygen using thermal conduction changes in connection with paramagnetism is described in U.S. Pat. No. 6,430,987B1.

In medical technology, complex fresh gas mixtures are sometimes used to ventilate patients under anesthesia. In most cases, these mixtures contain a binary basic mixture of oxygen and nitrogen and, if necessary, nitrous oxide and one of the common inhalation anesthetics (e.g. desflurane, sevoflurane, isoflurane, enflurane, halothane). For the monitoring of patients it is often necessary to also determine the gas concentrations during the expiratory phase of the patient. In the expiratory phase, the gas mixture contains, in addition to the gases mentioned, carbon dioxide, water vapor and possibly other metabolic products, such as ethanol, methane and acetone. With regard to the relevant gas concentrations, the interest is mainly limited to oxygen, carbon dioxide, nitrous oxide and the anesthetic as well as their temporal dynamics, if applicable. In the inspiratory phase, on the other hand, the gas mixture usually does not contain significant amounts of carbon dioxide. Usually, to determine anesthetic gas concentrations, concentrations of carbon dioxide, nitrous oxide and oxygen, several additional measuring devices with optical or electrochemical sensors that are independent and optimized for the respective target gas are used, to which the gas samples of the respiratory gas are fed simultaneously in parallel or sequentially in a serial manner. The measurements of such measuring devices must then be adjusted or synchronized with each other with regard to the temporal dynamics and the differences or conditions during the supply of the gas samples in order to determine the gas composition with regard to the situation actually present in a gas volume on the patient of concentrations or changes in concentrations of, for example, oxygen content determined by means of paramagnetism in one measuring device and infrared-optical in another measuring device. The measurement of the carbon dioxide, nitrous oxide and anesthetic gas content is carried out in a further measuring device.

SUMMARY

Based on the prior art, there is therefore a need for low-cost measurement systems, which are capable of detecting a concentration of oxygen and another gas, in particular an anesthetic gas in a gas mixture in a common gas sample of breathing gas.

The present invention is therefore based on the object of providing a measuring system, as well as a process, for determining both a concentration of oxygen and a concentration of a further gas, in particular an anesthetic gas in a gas mixture, in a common gas sample of respiratory gas, and thus overcoming the above-mentioned disadvantages when combining at least two measuring systems.

The object is attained by the features according to the invention. The object is attained by a measuring system having features according to the invention, and also by a process having features according to the invention.

Further features and details of the invention result from this disclosure including the description and the drawings. Features and details described in connection with the measuring system according to the invention naturally also apply in connection with the process according to the invention and vice versa in each case, so that reference is or can always be made mutually with regard to the disclosure of the individual aspects of the invention.

In accordance with a first aspect of the invention, embodiments are disclosed, with a measuring system comprising at least the following components:

A measuring device with a measuring element in a measuring chamber, with a gas supply (gas inlet) and a gas outlet, with an electromagnet and with a coil,
a calculation and control unit,
a circuit arrangement.

The calculation and control unit is configured to detect thermoelectric voltage signals of the measuring device provided by the measuring element.

The calculation and control unit is configured to divide the thermoelectric voltage signals into AC voltage signal components $U_{X\sim}$ and DC voltage signal components $U_{X=}$.

The alternating voltage signal components $U_{X\sim}$ and direct voltage signal components $U_{X=}$ can be symbolized and/or illustrated for different gases and gas mixtures of different moisture content and different temperatures as alternating voltage signal components $U_{X1\sim}$ to $U_{Xn\sim}$, or $U_{X1F\sim}$ to $U_{XFn\sim}$, and DC signal components $U_{X1=}$ to $U_{Xn=}$, or $U_{X1F=}$ to $U_{XFn=}$, as is also shown schematically by way of example in FIG. 5 for four dry and four moist gas mixtures, the index "F" denoting moist gas mixtures. For standardized (normalized) signals, the symbols $U_{Y\sim}$, $U_{YF\sim}$, and $U_{Y=}$, $U_{YF=}$ are used in this patent application. For pressure-compensated, standardized signals, the symbols $U_{Z\sim}$, $U_{ZF\sim}$, or $U_{Z=}$, $U_{ZF=}$ are used in this patent application.

The calculation and control unit is configured to standardize the AC voltage signal components $U_{X\sim}$ into standardized AC voltage signal components $U_{Y\sim}$.

The calculation and control unit is configured to standardize the DC voltage signal components $U_{X=}$ into standardized DC voltage signal components $U_{Y=}$.

The calculation and control unit is configured to standardize the standardized AC voltage signal components $U_{Y\sim}$ into standardized pressure-compensated AC voltage signal components $U_{Z\sim}$. The calculation and control unit is configured to determine an oxygen concentration in the gas mixture of the gas sample on the basis of the standardized AC voltage signal components $U_{Y\sim}$ or on the basis of the standardized pressure-compensated AC voltage signal components $U_{Z\sim}$.

The calculation and control unit is configured to determine a concentration of a further gas in the gas mixture of the gas sample on the basis of the standardized DC signal components $U_{y=}$.

In a preferred embodiment, the calculation and control unit can be configured to standardize the standardized DC voltage signal components $U_{Y=}$ into standardized pressure-compensated DC voltage signal components $U_{Z=}$. In a preferred embodiment, the calculation and control unit can be configured to determine a concentration of a further gas in the gas mixture of the gas sample based on the standardized pressure-compensated DC voltage signal components $U_{Z=}$.

The calculation and control unit is configured and adapted to provide an output signal indicating the determined oxygen concentration and the determined concentration of another gas in the gas mixture of the gas sample.

The measuring element is configured as a planar semiconductor or silicon element (MEMS, semiconductor chip) with a membrane and has a heating structure on the membrane and a heat conduction measuring unit at a measuring point.

The measuring device is configured together with the circuit arrangement for heating the heating structure on the membrane of the measuring element. The measuring element is arranged in the measuring chamber in such a way that a quantity of the gas mixture of the gas sample can be supplied to the measuring element. The measuring element is heated to an increased working temperature compared to the temperature of the quantity of the gas mixture in the measuring chamber. The measuring device is formed with the electromagnet, the coil and the circuit arrangement for generating a magnetic field acting on the measuring element. In the presence of a paramagnetic gas in the gas mixture at the measuring element, the heat conduction changes under the influence of the magnetic field in proportion to the proportion of the paramagnetic gas. For example, if oxygen is present in the gas mixture, a temperature increase occurs which results in an increase in the thermo-voltage signals detectable at the heated measuring element. The circuit arrangement is configured to provide measured values with an AC voltage signal component and with a DC voltage signal component to the calculation and control unit. With regard to the design of the operation by means of the calculation and control unit and further electronic components, in particular with monitoring, controlling and regulating the temperature of the measuring element, for example with a constant heating voltage, with a constant heating current, with a constant heating power and also with regard to the type of measured value acquisition which is dependent on and connected with this, various possibilities are shown by means of embodiments, supplemented by figures and their description.

The gas supply is configured to supply a quantity of a gas mixture of a gas sample to the measuring element. This gas supply can be configured to supply the quantity of the gas mixture of the gas sample by means of a supply line from an expiratory measuring location, an inspiratory measuring location, by means of a supply line from a measuring location close to the patient or from a sampling point of the gas supply in an anesthesia device or ventilator. After analysis in the measuring device, the measuring gas can be fed away from the measuring device to a gas disposal system by means of a gas transport system or, for example, can be fed back into an anesthetic gas circuit of an anesthesia device at a suitable position.

In an optional embodiment of the measuring device, the calculation and control unit may be configured to heat the measuring chamber and/or the gas supply in the measuring device. To avoid condensation on or on the measuring element, it is advantageous to heat the measuring chamber, the gas supply, the measuring device and/or the measuring system. The temperature level of the heating is selected and controlled in such a way that it can be kept constantly above the internal temperature of an anesthetic gas measurement in normal clinical operation by means of a control or regulation system. The following typical temperature ranges may be mentioned: A typical temperature range of about 10° C. up to 50° C. can be assumed as the operating temperature range of the measuring system. In special situations, e.g. in tropical or subtropical areas, the temperature in the measuring system can sometimes exceed values of 55° C. From this, a typical temperature control level of the measuring device can be derived up to about 600 to allow temperature stabilization. A permanent temperature control of the measuring device to temperatures above 60° C. is on the one hand associated with an increased energy input, on the other hand permanent temperatures above 60° lead to premature ageing of components of the measuring device, such as electronic elements as well as the measuring elements. On the one hand, the temperature control to an almost constant temperature level reliably prevents condensate formation in the measuring device, and on the other hand it has the advantage that, as a rule, no additional measures are necessary for temperature compensation of the measured values, i.e. the AC voltage signal components or DC voltage signal components.

The calculation and control unit may be configured to include or compensate for environmental conditions affecting the physical properties of the gas mixture in the gas sample.

The signal components are standardized to reference values by the calculation and control unit. The reference values are assumed to be a measured value of the AC voltage signal components and DC voltage signal components for a condition in which dry gas with a concentration of 100% oxygen is supplied to the measuring device with the gas sample and thus the measuring element is also surrounded by a gas concentration of 100% oxygen. The reference value for the standardization can preferably be determined in measurement tests or in the course of a functional check of the measuring device with a test device which is configured to provide a dry test gas with an oxygen concentration of 100%. The data determined in this way serve as a basis for the data storage of reference values in a data memory which can be read out by the calculation and control unit. The reference values can then be used by the calculation and control unit for standardization.

Embodiments of the invention show, partly supported by illustrations in figures, such a measuring system or a process for determining gas concentrations in a gas mixture of a gas sample with a measuring device with a measuring element, with an electromagnet with a coil, with a calculation and control unit and with a circuit arrangement and with a magnetic field arrangement, preferably in the form of an electromagnet with a coil. The system and the process provide an oxygen concentration in the gas mixture of the gas sample on the basis of alternating voltage signal components and a concentration of a further gas in the gas mixture of the gas sample on the basis of direct voltage signal components.

In a particularly preferred embodiment, the calculation and control unit can also be configured to take into account, during the standardization and/or following the standardization of the measured values to the measured values of the AC voltage signal components and DC voltage signal components, particular heat conduction effects and heat dissipation effects which are caused by differences in the measuring elements. An example of such differences is a deviation between the measuring elements with respect to the membrane thickness of the measuring elements. Due to semiconductor manufacturing processes during the processing of semiconductor wafers, not all microstructured elements on a semiconductor wafer have an exactly identical thickness or structure of the membrane at the heat conduction measuring unit, at the measuring point and/or in the heating structure. The possibility of different thicknesses of the measuring elements, respectively of the membranes of the measuring elements, given by the manufacturing process, has an essential influence on the distribution between the heat transport by means of solid-state heat conduction within the measuring element and also the heat transport by means of mechanical connection and fixing points and electrical contacting in relation to the heat transport by means of heat dissipation to the gas mixture of the gas sample by means of heat conduction, heat radiation and convection. For this purpose, the calculation and control unit can determine, for example in the case of a gas with known heat conduction, such as pure nitrous oxide or pure oxygen, a correction value typical for the measuring device, consisting of membrane, heating structure and heat conduction measuring unit, for example a so-called "Cell Variation Factor" (CVF), which compensates for fluctuations in the membrane thickness. The "Cell Variation Factor" (CVF) serves to compensate for these effects of thermal conduction, which are specific to the respective measuring arrangement and are contained in the AC and DC signal components. For an operation of the measuring system with the measuring device with assurance of a high accuracy with respect to the concentration determination of the further gas, in particular anesthetic gas, it is therefore advantageous that the calculation and control unit can also carry out an adjustment with respect to the differences caused by the series dispersion of the measuring elements. An execution of such an adjustment is preferably carried out under reproducible conditions, i.e. with a dry test gas of known gas composition, for example 100% oxygen ($O_2$). In principle for example, and in addition to using dry oxygen, a concentration of 100% nitrous oxide ($N_2O$), nitrogen ($N_2$) or a noble gas, for example helium (He), may also be used for standardization and/or adjustment.

Such an adjustment with regard to the differences between different measuring elements due to the series dispersion of the measuring elements with regard to the heat-conducting and heat-dissipating properties can be carried out, for example, with a procedure with the step sequence outlined below:

1. Supply of one of the above test gases,
2. Operation of the measuring element with settings at the standard operating point,
3. Recording of the corresponding AC and DC measured values,
4. Optional repetition of steps 1-3 with other gases,
5. Comparisons of the measured values with standard values or with reference values, and
6. Determination of the correction factors In addition to the standardization to the dry gas mixture with a gas concentration of 100% oxygen and the adjustment with regard to the heat-conducting and heat-dissipating properties of the measuring elements, an adjustment, a compensation or also an adjustment of the measuring device or the measuring system can also be carried out by the calculation and control unit with regard to ambient secondary or boundary conditions. These environmental secondary or boundary conditions result from properties of the measurement signal acquisition, such as properties of the electronic components used in amplifier circuits (OP amps) or in filter circuits, properties of analog to digital converter circuits (A/D converters) or also indirect effects from the voltage supply, e.g. from rectifier circuits or power supply units. Such properties include, for example, frequency-dependent or other non-linearities of transmission or gain characteristics of electronic components of amplifier or filter circuits, noise, offsets, temperature-dependent drift effects, as well as effects that may be caused by series dispersion of components or by component aging during the product service life.

Embodiments further show how information, data or measured values indicative of a pressure level in the gas mixture of the gas sample can be used for determining the oxygen concentration, as well as determining the concentration of another gas in the gas mixture of the gas sample by the calculation and control unit. For this purpose, for example, a pressure sensor can be arranged in the measuring system or assigned to the measuring system, which is configured and intended to determine a pressure level in the gas mixture of the gas sample metrologically. The calculation and control unit is configured for a pressure compensation of the AC signal components. The pressure compensation is necessary for a determination of the oxygen concentration, since changes in the pressure conditions are noticeable as an influence on the density in the gas mixture of the gas sample and, in addition, the mobility or the spatial proximity of oxygen molecules to one another in the gas mixture of the gas sample is influenced by the pressure level of the gas mixture in the gas sample. This spatial proximity, or spatial distance, of oxygen molecules to each other affects the way of mobility and alignment of oxygen molecules in the magnetic field. Influencing the orientation of the oxygen molecules in the magnetic field by the pressure given in the gas mixture thus also affects the paramagnetic effect of thermal conductivity, which is proportional to the proportion of oxygen in the gas mixture. Therefore, pressure compensation of the AC signal components by the calculation and control unit is provided according to the invention. For this purpose, information or a pressure measured value representing the current pressure level in the gas mixture of the gas sample is used by the calculation and control unit for pressure compensation of the AC signal components. Such a pressure measured value can be provided, for example, by a pressure sensor, which can be arranged in the gas supply, in the gas outlet or at the measuring element in the measuring device, in order to detect a pressure level in the gas mixture of the gas sample, which is representative in terms of location and time for a pressure compensation.

Embodiments further show how information, data or measured values indicative of a temperature level in the gas mixture of the gas sample can be used for determining the oxygen concentration, as well as determining the concentration of another gas in the gas mixture of the gas sample by the calculation and control unit.

In a preferred embodiment, the calculation and control unit is configured for temperature compensation of the AC voltage signal components.

In a preferred embodiment, the calculation and control unit is configured for temperature compensation of the DC voltage signal components.

The temperature compensation of the DC or AC signal components can be performed by the calculation and control unit in such a way that information or a temperature measured value representing the current temperature level in the gas mixture of the gas sample is used for the temperature of the signal components. Such a temperature measured value can be provided, for example, by a temperature sensor which can be arranged in the gas supply, in the gas outlet or at the measuring element in the measuring device in order to detect a temperature signal—which is locationally and temporally representative for a temperature compensation—in the gas mixture of the gas sample. For this purpose, for example, a temperature sensor can be arranged in the measuring system or assigned to the measuring system, which is configured and intended to determine a temperature in the gas mixture of the gas sample by measurement.

Embodiments further show how information, data, or measured values indicative of moisture in the gas mixture of the gas sample can be used for determining the oxygen concentration, as well as determining the concentration of another gas in the gas mixture of the gas sample by the calculation and control unit.

In a preferred embodiment, the calculation and control unit is configured for moisture compensation of the AC signal components.

In a preferred embodiment, the calculation and control unit is configured for moisture compensation of the DC signal components.

The moisture compensation of the DC or AC signal components can be carried out by the calculation and control unit in such a way that an information or a moisture measurement value representing the actual moisture level in the gas mixture of the gas sample is used for moisture compensation of the signal components. Such a moisture measured value can, for example, be provided by a moisture sensor which can be arranged in the gas supply, in the gas outlet or at the measuring element in the measuring device in order to detect a moisture level in the gas mixture of the gas sample which is representative of moisture compensation in terms of location and time. For this purpose, for example, a moisture sensor (humidity sensor) can be arranged in the measuring system or assigned to the measuring system, which is configured and intended to determine a moisture in the gas mixture of the gas sample by measurement.

A temperature sensor may be embedded on or in the moisture sensor to determine both the absolute and relative humidity in the gas mixture of the gas sample and thus determine the percentage by volume fraction of water or water vapor in the gas mixture of the gas sample for inclusion in the determination of the concentration of oxygen and the concentration of at least one other gas, particularly an anesthetic gas concentration. By way of illustration, here is what the situation would be like for determining the concentrations of oxygen and one other gas in the absence of moisture compensation. In a considered exemplary temperature range of 20° C.+/−10° C. and a pressure range of 1013 hPa+/−10 hPa for the gas mixture of the gas sample, there is an influence of the moisture in the range from dry gas to saturated steam, which can become noticeable, for example, in a deviation of the calculated oxygen concentration in the range from about 1.5% to 3.0% and can become noticeable in a deviation of the calculated concentration of, for example, desflurane in the range from about 10% to 15%.

In a preferred embodiment, the calculation and control unit can be configured to stabilize the temperature of the measuring device. The temperature stabilization can be carried out by the calculation and control unit in such a way that information or a temperature—measured value, which represents the current temperature level in the gas mixture of the gas sample, is used. For this purpose, for example, a temperature sensor may be arranged in the measuring system or associated with the measuring system, which is configured and intended to determine a temperature level in the gas mixture of the gas sample by measurement. Such a temperature sensor can be located in the gas supply (gas inlet), in the gas outlet or at the measuring element in the measuring device. Such a temperature sensor can be used for monitoring, controlling or regulating a temperature stabilization of the gas sample and the measuring element. On the one hand, such a temperature stabilization is required in order to detect the heat conduction of the gas mixture of the gas sample with the thermoelectric measuring element free of fluctuations or drift effects due to the ambient temperature in an unaltered manner, and on the other hand, a temperature stabilization with temperature control is performed in order to prevent condensation of the gas sample at the measuring element. Thus, for a detection of concentrations of a gas sample of exhaled gas, a stabilization to a temperature level above 37° C. should be carried out in order to reliably prevent condensation. Since under special ambient conditions, i.e. at ambient temperatures above 50° C., temperatures above 60° C. can occur inside the measuring system due to self-heating and only limited possibilities of heat dissipation from the measuring system to the environment, a temperature compensation of the ambient temperature or device temperature can be provided in embodiments. In a preferred embodiment, temperature compensation may be provided in such a way that a first set of data with reference values—based on measured values with 100% dry oxygen with a reference temperature of, for example, about 50° C.—is used for standardization for use within the temperature control level of the measuring device of 45° C. to 60° C. and a second set of data with reference values—based on measured values with 100% dry oxygen with a reference temperature of, for example, 65° C.—is used for use in ambient temperature ranges above the typical temperature control level of the measuring device of, for example, 60° C. In such embodiments, temperature compensation may be performed by the calculation and control unit using the measured values of the temperature sensor and the reference values of the first and second data sets of reference values, wherein interpolation may be performed by the calculation and control unit for temperature measured values between the reference temperature of the first data set and the reference temperature of the second data set, as well as for temperatures above the reference temperature of the second data set.

To illustrate this, the situation for the determination of the concentrations of oxygen and another gas without temperature compensation in an ambient temperature range above the reference temperature of the temperature control of the measuring device of approx. 65° C. may be considered. In a temperature range above 70° C.+/−10° C. and a pressure range of 1013 hPa+/−10 hPa for the gas mixture of the gas sample, there is a residual influence of temperature which may be noticeable, for example, in a deviation of the calculated oxygen concentration in the range of about 0.7% to 1.3% and may be noticeable in a deviation of the calculated concentration of, for example, desflurane in the range of about 10% to 15%. To estimate the significance of the moisture compensation, it can be stated as an estimate that an incorrect temperature compensation of 9° C. would have a similar influence on the concentration determination as an absolute humidity incorrectly compensated by 3 vol. %.

In a preferred embodiment, the calculation and control unit can be configured for pressure compensation of the standardized DC voltage signal components $U_{Y=}$ into standardized AC voltage signal components $U_{Z\sim}$. Such a pressure compensation of the direct voltage signal components or of the standardized direct voltage signal components makes it possible to compensate for differences in the density and thus in the thermal conductivity of the gas mixture of the gas sample. Differences in density arise, for example, in an area of application at high altitudes, such as at altitudes of more than 2500 meters, for example, in mountains or in aircraft, especially if additional negative pressure must be applied compared to the environment by suction sampling.

Embodiments further show how a moisture sensor can be arranged at a suitable position in the measuring system, in the measuring device or on the measuring element, in order to make it possible to detect a measured value representative of the moisture of the gas mixture in the gas sample with such a moisture sensor.

Embodiments further show how a purge chamber can be arranged in the measuring device. The arrangement of the purge chamber on the measuring element, in relation to the measuring element or in relation to the gas flow can preferably be such that the flowing gas mixture of the gas sample can flow into and through the purge chamber after flowing around/over the surface of the membrane of the measuring element. It is advantageous if the position of the moisture sensor is configured in the measuring device in such a way that the measured value is also representative of the situation of the flow with moisture in the gas mixture of the gas sample, for which also the alternating voltage signal components and direct voltage signal components are determined and determined by the calculation and control unit, so that a compensation of the moisture is made possible correlated in time with respect to the oxygen concentration and/or the concentration of the further gas in the gas mixture of the gas sample. This results in the advantage that the temporal course of the oxygen concentration and/or the concentration of the further gas in the gas mixture of the gas sample can also be correctly determined with respect to respiratory phases, since temporal delays or shifts due to a disadvantageous positioning of the moisture sensor cannot be included in the moisture compensation. It is advantageous to position the moisture sensor in the purge chamber.

Embodiments further show how at least one temperature sensor can be arranged at a suitable position in the measuring system, in the measuring device or on the measuring element, in order to make it possible to detect a measurement signal or a representative measured value representative of the temperature of the gas mixture in the gas sample using a temperature sensor.

In this context, it is important and advantageous if the position of the at least one temperature sensor is configured in the measuring device in such a way that the measurement signal or the measured value is also representative of the situation of the flow with temperature of the gas mixture of the gas sample, for which the alternating voltage signal components and direct voltage signal components are also determined and determined by the calculation and control unit, so that compensation of the temperature is possible in a temporally correlated manner with respect to the oxygen concentration and/or the concentration of the further gas in the gas mixture of the gas sample. This results in the advantage that the temporal course of the oxygen concentration and/or the concentration of the further gas in the gas mixture of the gas sample can also be correctly determined with respect to breathing phases, since temporal delays or shifts due to a disadvantageous positioning of the temperature sensor cannot be included in the temperature compensation.

Embodiments further show how a moisture sensor and/or a further temperature sensor and/or a reference temperature sensor at a suitable position in the measurement system, can be arranged in the measuring device or on the measuring element, in particular in the purge chamber at a suitable position in the measuring system, in the measuring device or on the measuring element. Advantageously, the at least one temperature sensor is positioned in the measuring chamber or in the purge chamber in which the moisture sensor is also positioned. The purge chamber is arranged in the measuring device in such a way that the gas mixture of the gas sample provided by means of a sample line can flow around or flow around the sensors arranged in the purge chamber in a timely manner for the metrological detection of the thermo-voltage signals.

Embodiments further show how at least one, preferably two, resistance measuring elements is, or are, arranged in or on the purge chamber.

In one embodiment, at least one resistance measuring element may be arranged in the purge chamber such that an evaluation of the measured values of this resistance measuring element enables the calculation and control unit to determine a flow condition.

In a further preferred embodiment, two resistance measuring elements may be arranged in relation to each other in the purge chamber such that an evaluation of the measured values of these resistance measuring elements enables the calculation and control unit to determine a flow condition. This enables the calculation and control unit to distinguish whether there is a flow through the measuring device with a substantially continuous flow of the gas mixture of the gas sample in the measuring device with a flow over or around the measuring element, or whether there is a situation without a flow. Corresponding information indicating this flow condition in the measuring device may be generated and provided by the calculation and control unit. Such information indicating the flow condition in the measuring device may be provided by the two resistance measuring elements arranged in the gas inlet or gas outlet, for example in the form of resistance measuring elements or thermistors (negative temperature coefficient (NTC) temperature sensors). Advantageously, such an arrangement of the two resistance measuring elements or thermistors is provided when one of the two is exposed to the flow and the other is not exposed to the flow. A comparison of measured values of the two resistance measuring elements or thermistors with respect to each other then enables the calculation and control unit to detect a condition in which the resistance measured in the flow is not flowing around the resistance measuring element or the thermistor and, based on this comparison, to provide an output signal or error signal which indicates an error condition with respect to the flow, the gas supply and/or the gas outlet of the measuring device or the measuring system.

Embodiments further show a sensor measuring unit, which is used in the measuring device or in the measuring system for a detection of at least one of the measured values
- of the resistance measuring elements,
- of the pressure sensor,
- of the moisture sensor,
- at least one temperature sensor, and is assigned to the calculation and control unit and is configured and provided for providing the recorded measured values or data derived from the measured values to the calculation and control unit. The sensor measuring unit can be configured as an independent measuring module or as a sub-module of the calculation and control unit.

In embodiments, the measurement system samples, by means of the gas supply, a gas mixture:
- from a near-patient connection element (Y-piece) as a near-patient gas sample,
- from the expiratory feed line as an expiratory gas sample,
- from the inspiratory supply line as an inspiratory gas sample,
- from a sampling point of the gas line—e.g. at the point of the fresh gas feed—in the anesthesia or ventilation device as an internal gas sample, and by means of the calculation and control unit gas concentrations of oxygen and another gas in the gas sample can be determined.

Embodiments of the measuring system, as well as of the process, can be used both in the inspiratory (inhalation) phase and in the expiratory (exhalation) phase. For this purpose, it can be advantageous to use the measuring system in the inspiratory path, i.e. to be arranged in the gas-guiding connection from the anesthesia or ventilation device to the patient, for an inspiratory measurement. In this respect, it can also be advantageous to arrange the measuring system in the expiratory path, i.e. to be arranged in the gas-guiding connection from the patient to the anesthesia or ventilation device, for an expiratory measurement.

In embodiments in which the measuring system with the measuring device is used in the clinical environment of intensive care medicine or in an intensive care unit, for example in connection with a ventilator, the measuring system with the measuring device is usually not confronted with gas quantities of one anesthetic gas or several anesthetic gases in combination with nitrous oxide (nitrous oxide, $N_2O$). In such intensive medical embodiments, when by means of a ventilator, an anesthesia device or a system for inhalative sedation only one anesthetic gas (halothane, sevoflurane, enflurane, isoflurane, desflurane) is metered into the respiratory gas and the gas sample with a gas mixture is supplied to the measuring system by means of a measuring gas line from the inspiratory path of the intensive medical device, the calculation and control unit is able to determine a concentration of the anesthetic gas and a concentration of oxygen in the gas mixture of the gas sample, since in such a configuration no quantities of carbon dioxide are supplied to the measuring system. The concentration of the anesthetic gas and the concentration of oxygen in the gas mixture of the gas sample are determined by the calculation and control unit on the basis of the thermo-voltage signals for such an intensive medical application in the following manner:

a) Signal separation of the thermo-voltage signals into a DC voltage signal component and an AC voltage signal component.

b) Optional moisture compensation using readings from a moisture sensor or information indicating a moisture content in the gas mixture of the gas sample.

c) Standardization of the AC voltage signal components $U_{X\sim}$ and DC voltage signal components $U_{X=}$ to reference values and conversion into standardized AC voltage signal components $U_{Y\sim}$ and standardized DC voltage signal components $U_{Y=}$, d) Pressure compensation of the standardized AC signal components $U_{Y\sim}$ using the measured values of a pressure sensor or information indicating the current pressure level in the gas mixture of the gas sample.

e) Determination of an oxygen concentration in the gas mixture of the gas sample on the basis of the pressure-compensated, standardized alternating voltage signal components $U_{Z\sim}$ f) Determination of an anesthetic gas concentration in the gas mixture of the gas sample on the basis of the standardized DC signal components $U_{Y=}$ g) providing an output signal indicating the concentration of another gas and the oxygen concentration in the gas mixture of the gas sample.

In a preferred embodiment, a previously determined correction value typical for the measuring device consisting of diaphragm, heating structure and heat conduction measuring unit, for example the "Cell Variation Factor" (CVF) for correcting the influence on the AC voltage and DC voltage signal components due to the manufacturing-related tolerances in the construction of the measuring element and measuring device can be carried out by the calculation and control unit in an intermediate step between steps d) and e).

Embodiments show further possible applications in which the measurement system with the measurement device can be used in a clinical environment outside clinical areas of intensive care, anesthesia, intensive care units, and emergency medicine. For example, embodiments can be configured for gas measurement technologies that can be used in process gas analysis, laboratory analysis, or environmental analysis. Embodiments further show how information provided regarding a gas composition of the gas mixture of the gas sample may be included in the determination of the further gas concentration and/or the oxygen concentration.

If in an application of the measuring system it cannot be ensured that no amounts of an extraneous gas are contained in the gas mixture of the gas sample, it is advantageous if the calculation and control unit can include information regarding a gas composition of the gas mixture of the gas sample and the extraneous gas in the determination of the further gas concentration, preferably an anesthetic gas, and/or the determination of the oxygen concentration.

If, in an application of the measurement system, it cannot be ensured, for example, that no amounts of carbon dioxide are contained in the gas mixture of the gas sample, it is advantageous if the calculation and control unit can include corresponding information regarding a gas composition of the gas mixture of the gas sample in the determination of the further gas concentration. For example, in application cases in which oxygen is not provided by means of a pressurized gas cylinder or hospital infrastructure as, as it were, pure oxygen, but by means of a concentration enrichment by means of pressure swing adsorption, the proportions of argon present in the oxygen as foreign gas may be several times higher. Information about the presence and concentrations of such foreign gases in the gas mixture, such as argon, for example, can—if provided to the calculation and control unit accordingly—be included by the calculation and control unit in the determination of the further gas concentration, preferably of an anesthetic gas, and/or the determination of the oxygen concentration. If oxygen, which is supplied by means of pressure swing adsorption, is used in a closed or semi-closed anesthesia breathing circuit system, the reuse of the exhaled gas in the circuit results in a further enrichment of argon in the breathing gas mixture, which is again fed back to the patient, since the lime absorber arranged in the circuit can remove the exhaled gas quantities of carbon dioxide from the breathing gas mixture which is fed back, but cannot reduce the gas quantities of argon in the circuit.

In a particular embodiment, a determination of the concentration of argon as a further gas in the gas mixture can also be determined by the calculation and control unit on the basis of the DC signal components. This applies, for example and in particular, to applications with monitoring of the gas composition in the field of intensive care medicine where no anesthetic gases and no nitrous oxide are contained in the gas mixture. However, this also applies to applications with monitoring of the gas composition in the field of anesthesia, where the concentrations of anesthetic gases and nitrous oxide in the gas mixture are known. In such applications, the measuring system can detect a concentration of argon as a further gas in addition to an oxygen concentration.

Embodiments further show how information provided regarding a gas composition of the gas mixture of the gas sample can be included in the determination of the oxygen concentration. If, for example, in an application of the measurement system, it cannot be ensured that no quantities of a further paramagnetic gas, for example nitrogen oxide (NO), nitrogen dioxide ($NO_2$), chlorine dioxide ($ClO_2$), are contained in the gas mixture of the gas sample, it is advantageous if the calculation and control unit can include information relating to a gas composition of the gas mixture of the gas sample in the determination of the oxygen concentration.

Provided information regarding a gas composition of the gas mixture of the gas sample is, for example, data which is provided by a further or external system, for example by a measuring system which is used for monitoring a dosage of gas mixtures with several gases, in particular anesthetic gases, in or at the anesthesia device. Further data are, for example, data which are received from a further or external system, for example from a measuring system which is in use for monitoring an exhalation concentration of carbon dioxide (capnometry) in or on the anesthesia apparatus or ventilator. If, for example, the current concentration of carbon dioxide is provided to the calculation and control unit, the calculation and control unit is thus enabled to determine the oxygen concentration and the concentration of the further gas, in particular anesthetic gas, for the determination of the concentrations of the individual gas components in the gas mixture of the gas sample and to provide them in a common data set.

If, for example, the current concentration of a gas or of the additional gas is provided to the calculation and control unit, the calculation and control unit is thus enabled to determine the oxygen concentration, the concentration of the additional gas, in particular anesthetic gas, and the concentration of the additional gas in the gas mixture of the gas sample and to provide them in a common data set.

Embodiments further show how information provided with respect to a dosing state of a dosing (metering) system may be included in the determination of the oxygen concentration and/or in the determination of the further gas concentration.

In such embodiments, the calculation and control unit is configured to,
provide information regarding a dosing state of a dosing system,
provide information in relation to respiratory phases
provide information in relation to operating conditions of an anesthetic or respiratory machine.

The calculation and control unit can then proceed with the information regarding a gas composition of the gas mixture of the gas sample in the same way as in the embodiments in which information and data provided regarding a gas composition of the gas sample are used to determine the oxygen concentration and/or the further gas concentration.

In particularly preferred embodiments, the calculation and control unit can provide the determined gas concentration of the further gas by means of data interface as information to another or external system for determining anesthetic gas concentrations, for example to an anesthetic gas metering device. Thus, in cases of application in which, from a safety point of view, two substantially redundant or independent pieces of information regarding a concentration of a particular anesthetic gas are to be available, the anesthetic gas concentration determined by the calculation and control unit can be used by the anesthetic gas measuring device for checking the plausibility of the measured values or for functional testing. Conversely, such a possibility of checking for plausibility or function also exists for the calculation and control unit if an external system provides, by means of a data interface, data or information indicating the gas concentration of the further gas, in particular anesthetic gas, to the measuring system according to the invention. Then, the calculation and control unit can check the function of the measuring system, for example, whether an actual gas mixture is conveyed to the measuring device through the measuring gas line and whether the thermo-voltage signals with DC signal component and AC signal component are plausible with respect to the flow situation and/or the information provided by the external system. Use cases in which two essentially redundant or independent pieces of information may be required from a safety point of view, can be formed by dosing systems for gases, in particular dosing systems for anesthetic gases and mixing systems for breathing gases with closed-loop control. Such dosing systems can be implemented by the concentration of the further gas being additionally provided by the measuring system according to the invention.

In accordance with a further aspect of the invention, a process according to the invention for a determination of gas concentrations in a gas mixture of a gas sample is described below. Gas mixtures with portions of water or water vapor, i.e. with moisture, are referred to in the context of the present invention as "moist gas mixtures".

The process makes it possible to determine an oxygen concentration and an anesthetic gas using measured values with an alternating voltage signal component $U_{X\sim}$ and with a direct voltage signal component $U_{X=}$. In the process according to the invention, a calculation and control unit—or another unit suitably configured for carrying out process steps—carries out the process steps listed below which are necessary for determining the gas concentration of the further gas and for determining the oxygen concentration:

a) Signal separation of the thermo-voltage signals into a DC voltage signal component and an AC voltage signal component.
b) Standardization of the AC voltage signal components $U_{X\sim}$ and DC voltage signal components $U_{X=}$ to reference values and conversion to standardized AC voltage signal components and standardized DC voltage signal components $U_{X=}$,
c) Pressure compensation of the standardized AC signal components $U_{Y\sim}$ using the measured values of a pressure sensor or information indicating the current pressure level in the gas mixture of the gas sample,
d) Determination of an oxygen concentration in the gas mixture of the gas sample on the basis of the pressure-compensated, standardized alternating voltage signal components $U_{Z\sim}$,
e) Determination of an anesthetic gas concentration in the gas mixture of the gas sample based on the standardized DC signal components $U_{Y=}$,
f) providing an output signal indicating the concentration of another gas and the oxygen concentration in the gas mixture of the gas sample.

In a further step, preferably following step a) or step b), an optional moisture compensation may be performed by including readings from a moisture sensor or information indicative of a moisture content in the gas mixture of the gas sample. The optional moisture compensation described in this further step is required in gas mixtures with variable proportions of moisture, for example when inhaled or exhaled gas mixtures are analyzed using the process according to the invention. This is the case, for example, in anesthesia applications where the process is used to determine an oxygen concentration and an anesthetic gas concentration. In applications in which an analysis of defined dry gas mixtures is required, for example for the analysis of dry inhalation gas or fresh gas in a respirator which does not have any recirculation of exhalation gases into the inhalation gas, compensation of the moisture—and thus also a moisture sensor—can be dispensed with.

Furthermore, according to the further aspect of the invention, for the process according to the invention an extension of the procedure for an adjustment of the measuring device with respect to possible differences of the measuring elements based on a series dispersion in the heat-conducting and heat-dissipating properties is described in a step sequence. It is advantageous to embed these steps for adjusting the heat-conducting and heat-dissipating properties of the measuring elements in the process according to the invention for a determination of gas concentrations in a gas mixture of a gas sample, preferably as a step between process steps d) and e) or between process steps e) and f). In such a step, an adjustment or correction of the influence on the AC voltage and/or DC voltage signal components by the manufacturing-related tolerances in the structure of the measuring cell takes place. In order to determine such tolerances in the construction of the measuring cell, the heat-conducting and heat-dissipating properties of the measuring element and effects which are based on series dispersion, for example on differences in the membrane thickness of the measuring elements, are determined by series of measurements under reproducible conditions, i.e. with a dry test gas of known gas composition, and are then stored in correction data records which are then used during operation of the measuring system when determining the gas concentration of the further gas and when determining the oxygen concentration.

The measuring system according to the invention and the process according to the invention exploit the advantage, in particular in the case of inspiratory measurement using a ventilator, that neither carbon dioxide nor nitrous oxide are used as anesthetic agents. In such a configuration, the measuring system or process according to the invention can advantageously, i.e. without further additional measuring devices or sensors, detect both the oxygen concentration and the anesthetic gas concentration of at least one anesthetic gas. Also, when using the measuring system according to the invention or the process in, on or with an anesthesia device, the advantage arises that, if no nitrous oxide is used, due to the ventilation circuit with $CO_2$ absorber there is also no carbon dioxide present in the gas mixture and thus a comparable situation arises as for use on a ventilator. For expiratory measurements or near-patient measurements, for the use of the measuring system or process according to the invention, or process then information provided by the ventilator or anesthesia device or further measuring devices with respect to the respiratory phases, or assumptions, measurement signals, measured values or information on the carbon dioxide concentration can be used to determine the oxygen concentration and the anesthetic gas concentration. The measuring system according to the invention and the process according to the invention thus offer a cost-effective and practical solution for monitoring the dosage of gas concentrations (oxygen, anesthetic gas) for applications in which anesthesia, anesthesia or volatile sedation is carried out without nitrous oxide, which is already currently the case in more than 90% of the anesthesia procedures carried out. In addition, the measuring system according to the invention and the process according to the invention offer a practical solution for monitoring the dosage of gas concentrations (oxygen, anesthetic gas) also for fields of application in the intensive care unit, when anesthetic gas is added to inspiratory gas or close to the patient.

With reference to the following description, and with partial reference to the figures, the invention will be explained in more detail. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
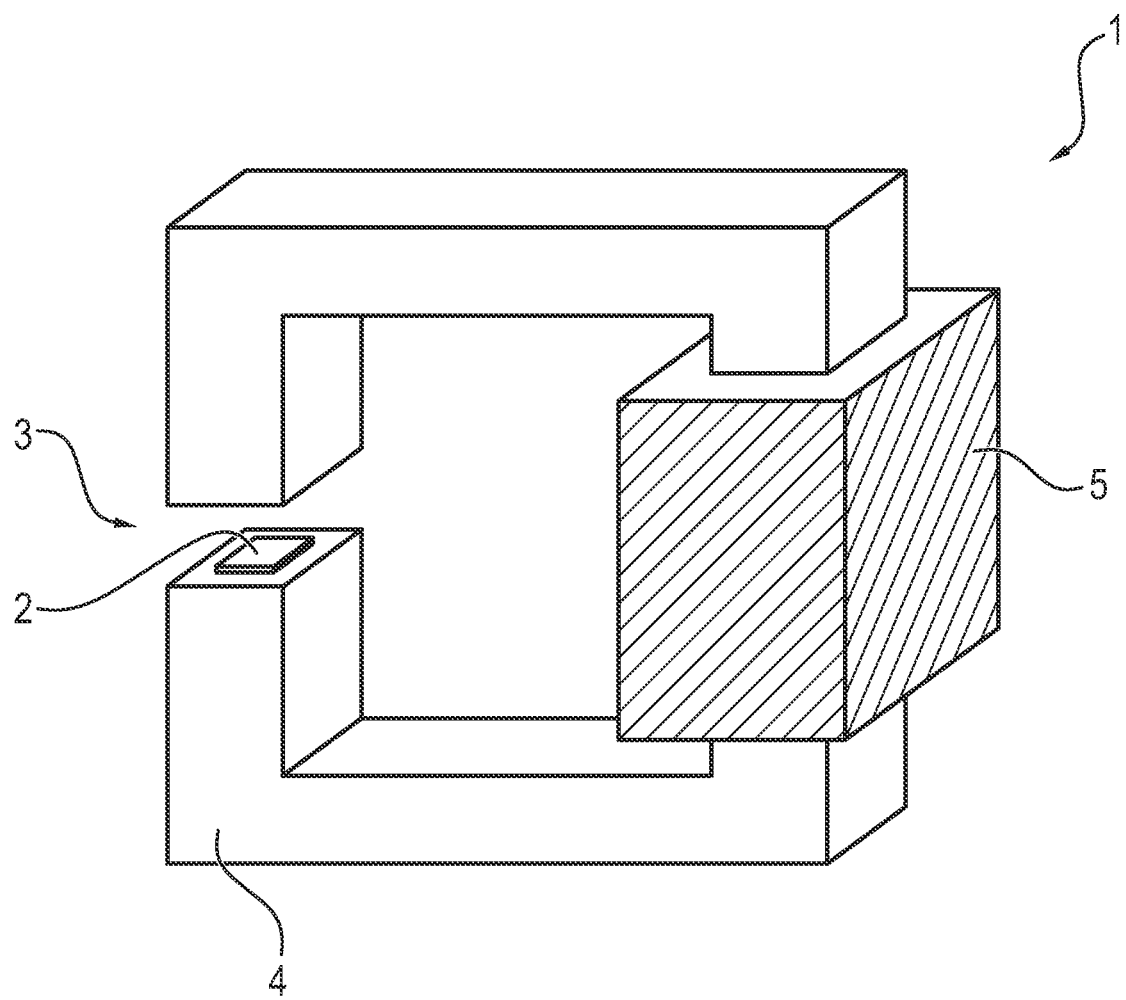
FIG. 1 is a schematic view showing a measuring device with an electromagnet having an air gap with a measuring element arranged therein.

Referring to the drawings, FIG. 1 shows a measuring device 1 with an electromagnet 4 with an air gap 3, in which a measuring element 2 is arranged. The measuring device (or sensor) 1 is intended and suitably configured for the metrological detection of an oxygen concentration or the concentration of another paramagnetic gas in a gas sample.

The gas guidance within the measuring device 1, for example in the form of designs of cuvettes or caverns (pockets), and also the gas guidance towards and away from the measuring device 1 is not shown in FIGS. 1 to 4 for reasons of clarity of the drawings. The measuring device 1 has a measuring element 2 which, in the case shown, is arranged in the air gap 3 of an electromagnet 4 provided with a coil 5, so that an electrically controllable magnetic field can be applied to the measuring point of the measuring element 2. Instead of the coil 5, in an alternative embodiment a permanent magnet (not shown) can also be provided, with the aid of which a constant magnetic field can be generated. The measuring device 1 is further configured to allow the gas to be analyzed to flow as a gas sample through the air gap 3 and past the measuring element 2.

Figure 2:
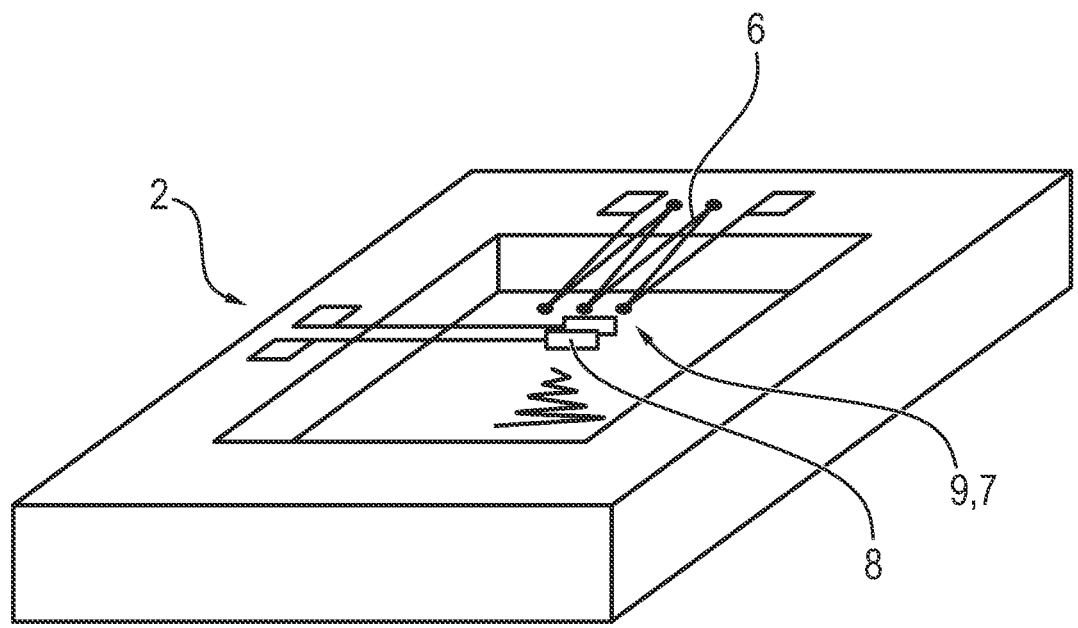
FIG. 2 is a schematic view showing a representation of the measuring element according to FIG. 1.

In FIG. 2 it is shown that the measuring element 2 has a measuring point with a heat conduction measuring unit 6, which is configured as a thermocouple (thermopile). The measuring element 2 may comprise one or more heat conduction measuring units 6. The measuring element 2 may comprise an at least partially perforated membrane 7 for the gas sample to enter from the upper side and/or the lower side. Preferably, however, a closed membrane 7 is used, the support frame of which has been removed, for example by etching, to the extent that the sample gas can pass under the membrane through the resulting gap. In order to allow access of the measuring gas to be analyzed to both sides of the measuring point 9, either the membrane 7 can be partially removed by etching, or the measuring element 2 is partially etched thinly in such a way that the gas access from the front is possible. Preferably, the magnetic field generated by the coil 5 is implemented as a pure alternating field with a time course symmetrical to the zero point. The time course is preferably sinusoidal, but may also have other shapes (for example triangular or stepped rectangular shape). The magnetic field may alternatively or additionally be controlled in amplitude. The amplitude control of the alternating magnetic field results in the advantage of being able to simultaneously reduce the electrical power for the measuring points at higher oxygen signal levels with the magnetization. However, a magnetization with a DC component is also conceivable, in which the modulated field component can be shifted on the magnetization characteristic. In order to keep the energy input for the magnetization low, the magnetic field may be generated at least partially with a permanent magnet. As can further be seen in FIG. 2, the measuring element 2 has an electrically controllable heating structure 8, which can be configured, for example, as an electrically conductive resistance structure arranged on the membrane or as a heating wire. Preferably, the heating structure 8 is configured to heat the membrane 7 of the measuring element 2 to a desired temperature. It should be noted that the thermal conduction measuring unit 6 and the heating structure 8 may be integrally configured, i.e. a resistive heating/measuring element in which temperature measurement is enabled using the temperature coefficient of the resistive material. Examples of such heating structures 8 may comprise heating wires or similar heating means with a temperature-dependent resistivity. Consequently, if technically feasible, the measuring units 6 and the associated heating structures 8 can also be replaced by integrated temperature-dependent structures.

Figure 3A:
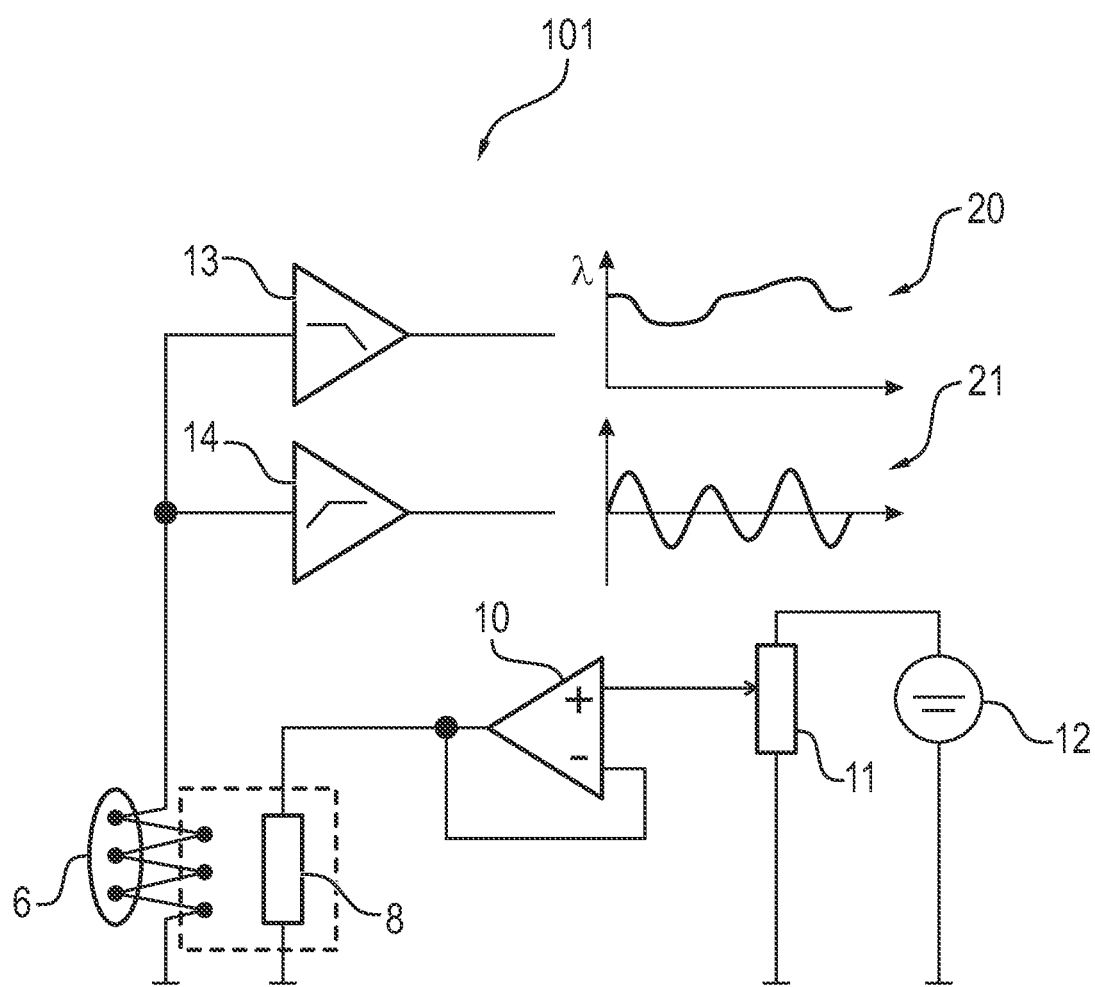
FIG. 3a is a schematic view showing a first variant of an electronic circuit for controlling the measuring point of FIG. 2 with the supply of a constant electrical voltage.
Figure 3B:
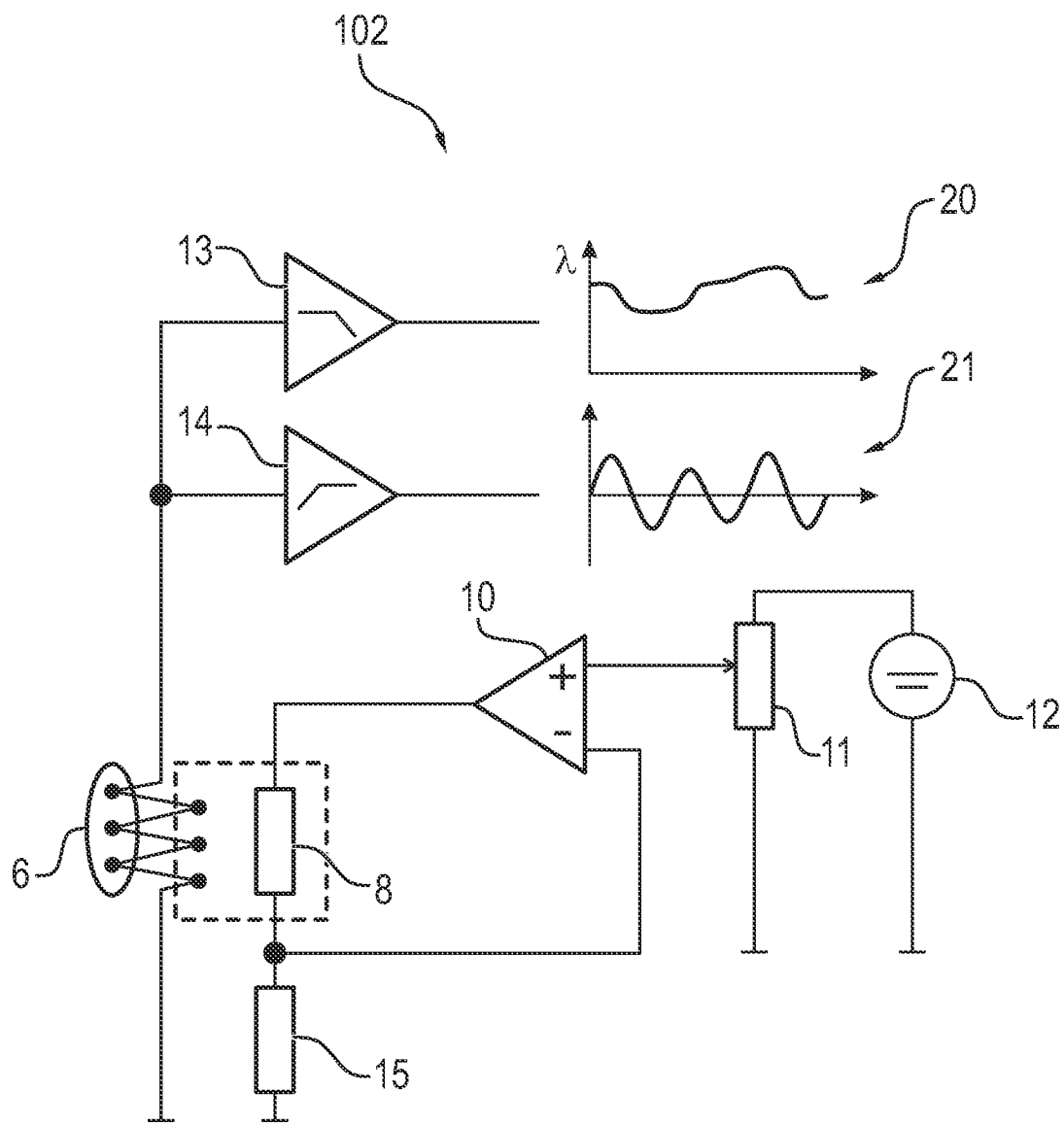
FIG. 3b is a schematic view showing a variant of an electronic circuit for controlling the measuring point with the supply of a constant electric current.
Figure 3C:
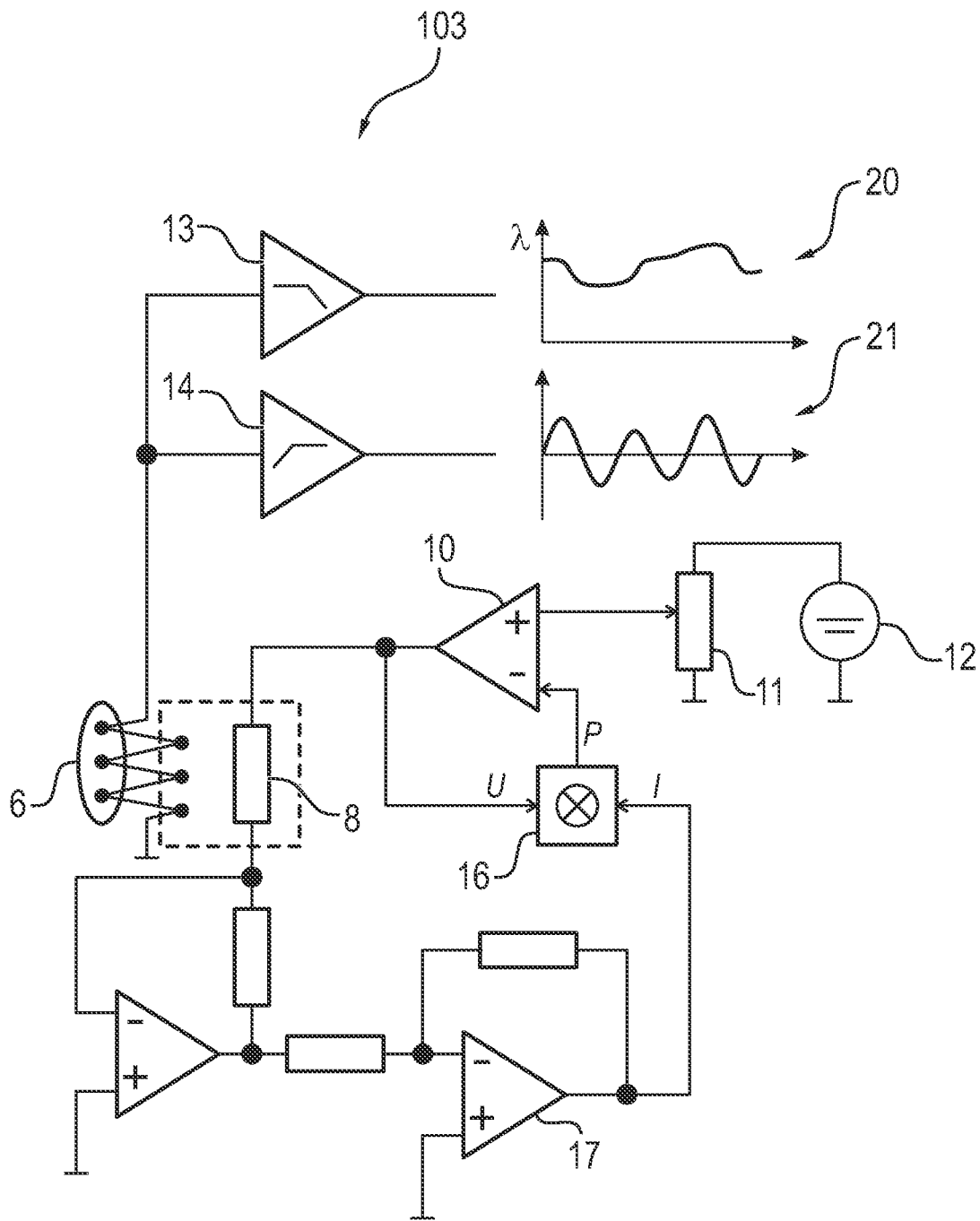
FIG. 3c is a schematic view showing a variant of an electronic circuit for controlling the measuring point with the supply of a constant electrical power.

In the figures, for reasons of clarity, these temperature-dependent heating structures 8 are shown separately and simplified as a heat conduction measuring unit 6 and a heating structure 8, respectively. The aspects described in the following description of the figures regarding operation and signal evaluation predominantly refer to arrangements with one measuring point and one measuring unit 6 arranged on one measuring element 2, unless otherwise mentioned, these aspects are thereby also transferable to arrangements with more than one measuring point and more than one measuring unit 6 arranged on one measuring element 2. In the following, operation and control of the heating structures 8 on the measuring element 2 will be described. In the type of control as shown in FIGS. 3a, 3b, 3c, the measuring point 9 is operated with a constant heating voltage (FIG. 3a), with a constant heating current (FIG. 3b) or with a constant heating power (FIG. 3c), which are adapted to the respective thermal operating point of the heating structure 8, the required values being determined once in a reference gas, e.g. oxygen or air, and then kept constant (calibration). The measured values for the thermal conduction 20 of the gas flowing past the measuring point 9 and the resulting periodic oxygen signals 21 can be found here in the voltages of the thermal conduction measuring unit 6.

FIGS. 3a to 3i show variants of the measuring device 1 with different circuit arrangements 101, 102, 103, 104, 105, 106, 107, 108, 109 for operating the measuring device 1. Identical elements in FIGS. 1, 2 and in FIGS. 3a, 3b, 3c, 3d, 3f, 3g 3h, 3i are designated by the same reference numerals in FIGS. 1, 2, 3a, 3b, 3c, 3d, 3f, 3g 3h, 3i.

FIG. 3a shows a schematic representation of an electronic circuit arrangement 101 for an operation of the measuring element 2 according to FIG. 2. In the circuit arrangement 101, the magnetizing device is not shown for simplification of the representation, and also the connection of the measuring points, of the heating structure 8, of the measuring element 2 and of the heat conduction measuring unit 6 is only shown simplified and schematically. On the one hand, the operation of the measuring element 2 comprises the configuration of the way of heating the measuring element 2. The heating of the measuring element 2 can be carried out with a constant heating voltage, with a constant heating current or with a constant heating power. By way of example, a control system with constant heating voltage is described with reference to this FIG. 3a. The heating structure 8 is connected to a DC voltage source 12 via an amplifier 10 connected as an impedance converter and a voltage divider 11 with variable tap. The elements 10, 11, 12 together form a constant voltage source. The measured value of the thermal conductivity measuring unit 6 is passed for evaluation through a low-pass arrangement 13 and through a high-pass arrangement 14. An alternating voltage signal component 21 is provided at the output of the high-pass arrangement 14. A direct voltage signal component 20 is provided at the output of the low-pass arrangement 13. The AC signal component 21 in the measured value represents an oxygen concentration in the gas composition of the gas sample. The DC signal component 20 in the measured value represents a thermal conductivity of the gas composition of the gas sample. Simple filtering devices can be used to remove fluctuations in the oxygen concentration that occur periodically in the gas sample from the measured value. With such simple filter circuits, signal components superimposed on the measured value, which are caused by electromagnetic radiation, for example from the 230V AC/50 Hz supply voltage network, can also be eliminated. To determine the oxygen concentration, the resulting periodic alternating voltage signal component and the non-periodic direct voltage signal component are related to each other and evaluated; the process of evaluation is further described in the description of FIGS. 4 and 5.

FIGS. 3b, 3c, 3d, 3e, 3f, 3g, 3h, 3i each show in schematic form further alternative embodiments 102, 103, 104, 105, 106, 107, 108, 109 of the electronic circuit arrangement 101 for operation of the measuring element 2 according to FIG. 2. Identical elements in FIGS. 1, 2 and in FIGS. 3a, 3b, 3c, 3d, 3f, 3g 3h, 3i are designated by the same reference numerals in FIGS. 1, 2, 3a, 3b, 3c, 3d, 3f, 3g 3h, 3i.

Figure 3D:
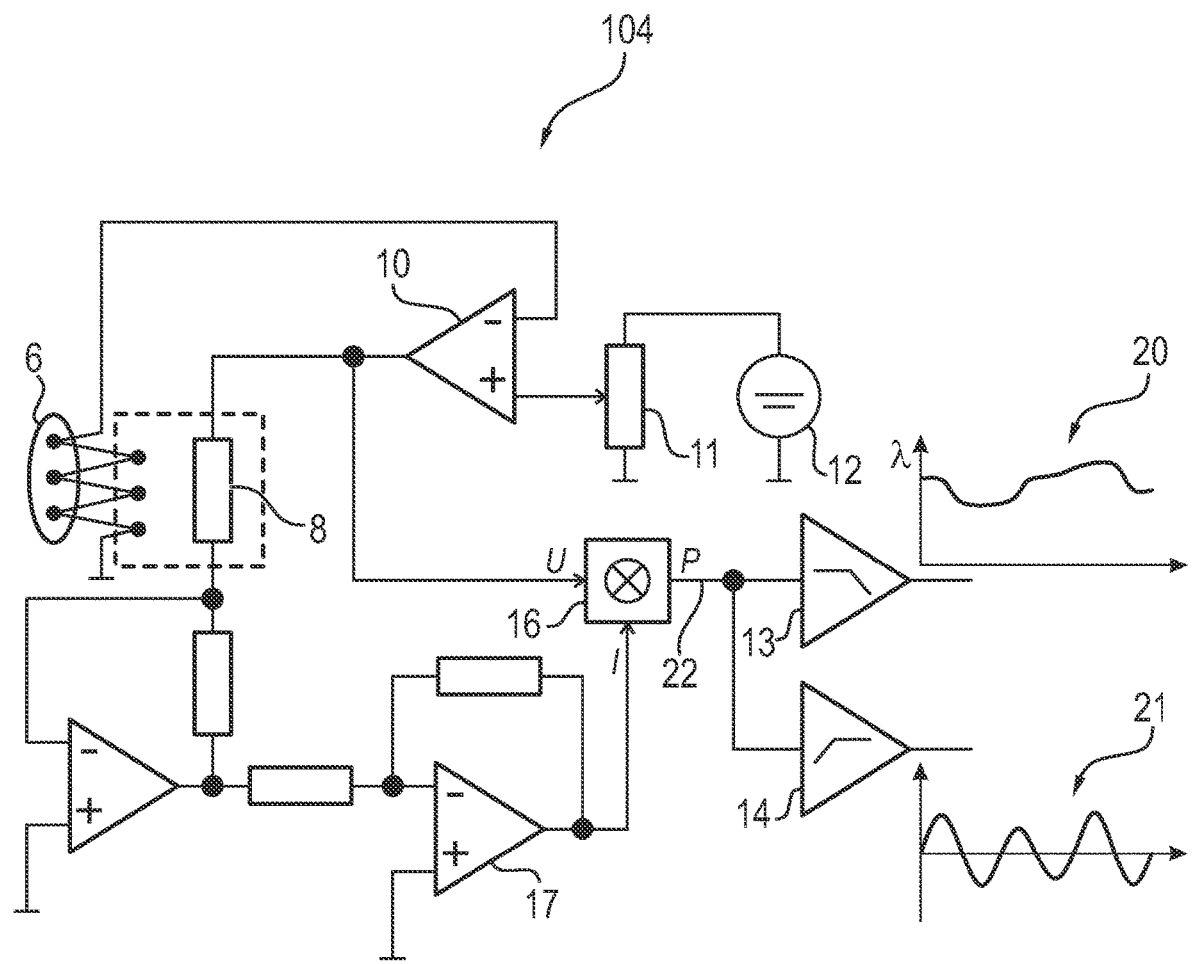
FIG. 3d is a schematic view showing a variant of an electronic circuit in which the heating power is used for temperature control.
Figure 3E:
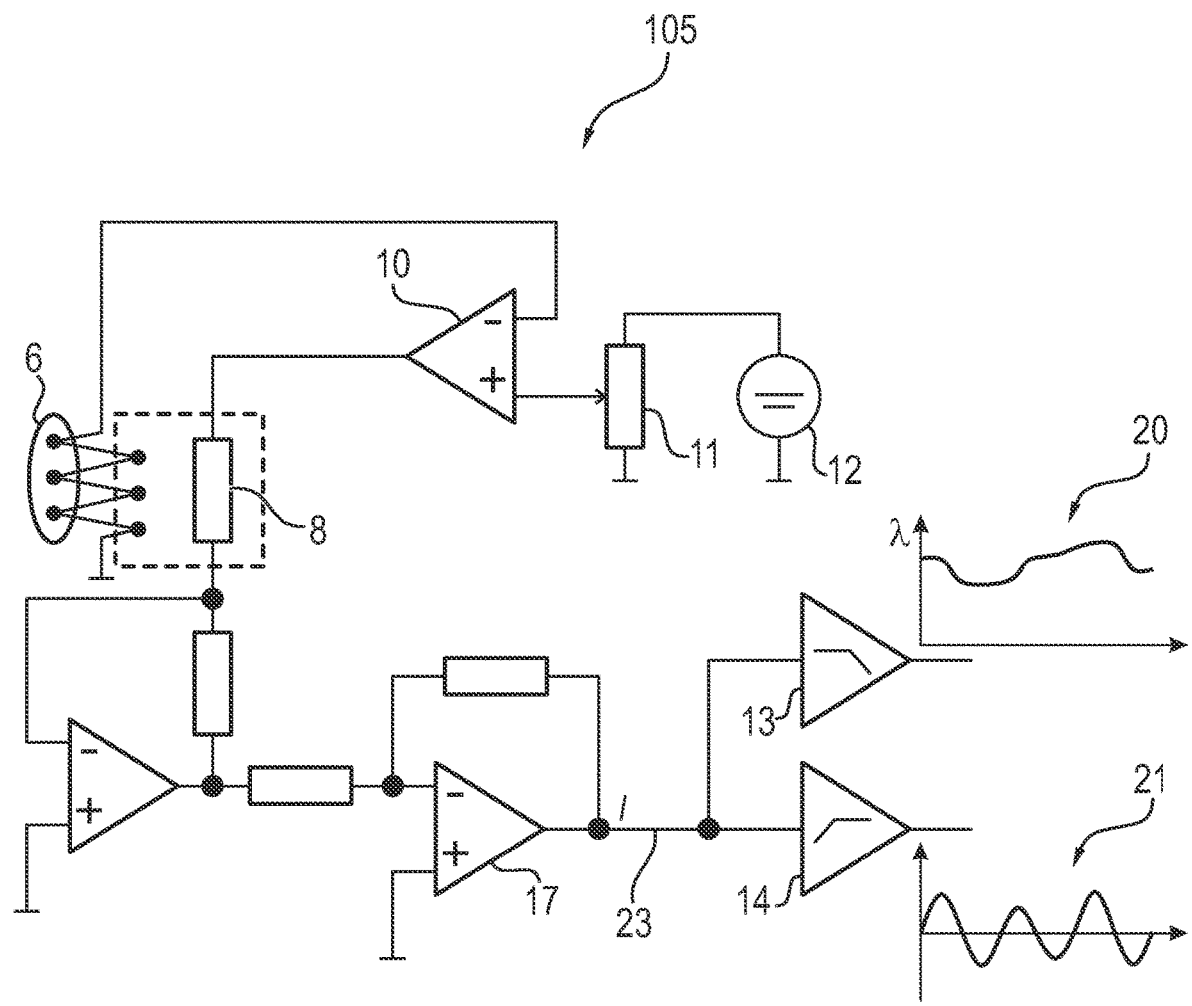
FIG. 3e is a schematic view showing a variant of an electronic circuit in which the heating current is used for temperature control.
Figure 3F:
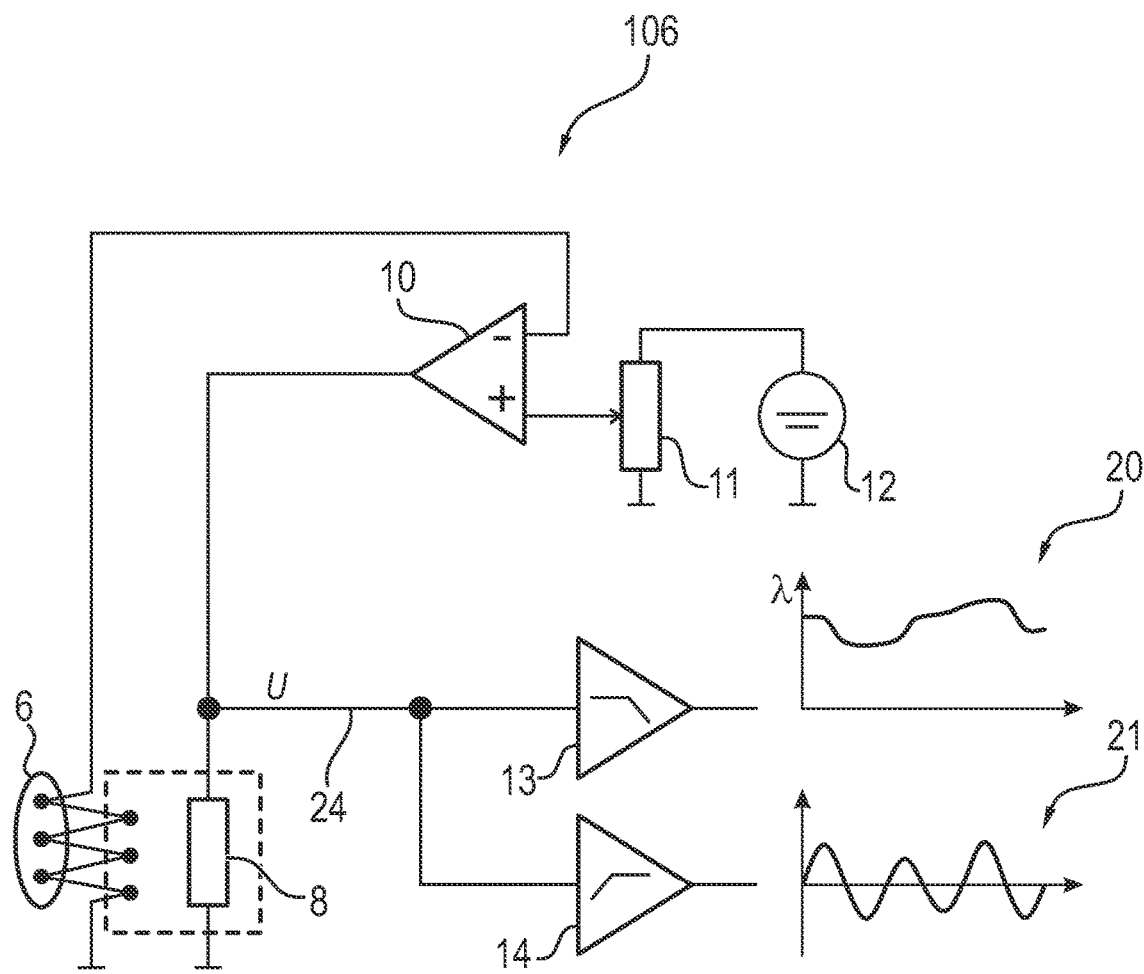
FIG. 3f is a schematic view showing a variant of an electronic circuit in which the heating voltage is used for temperature control.
Figure 3G:
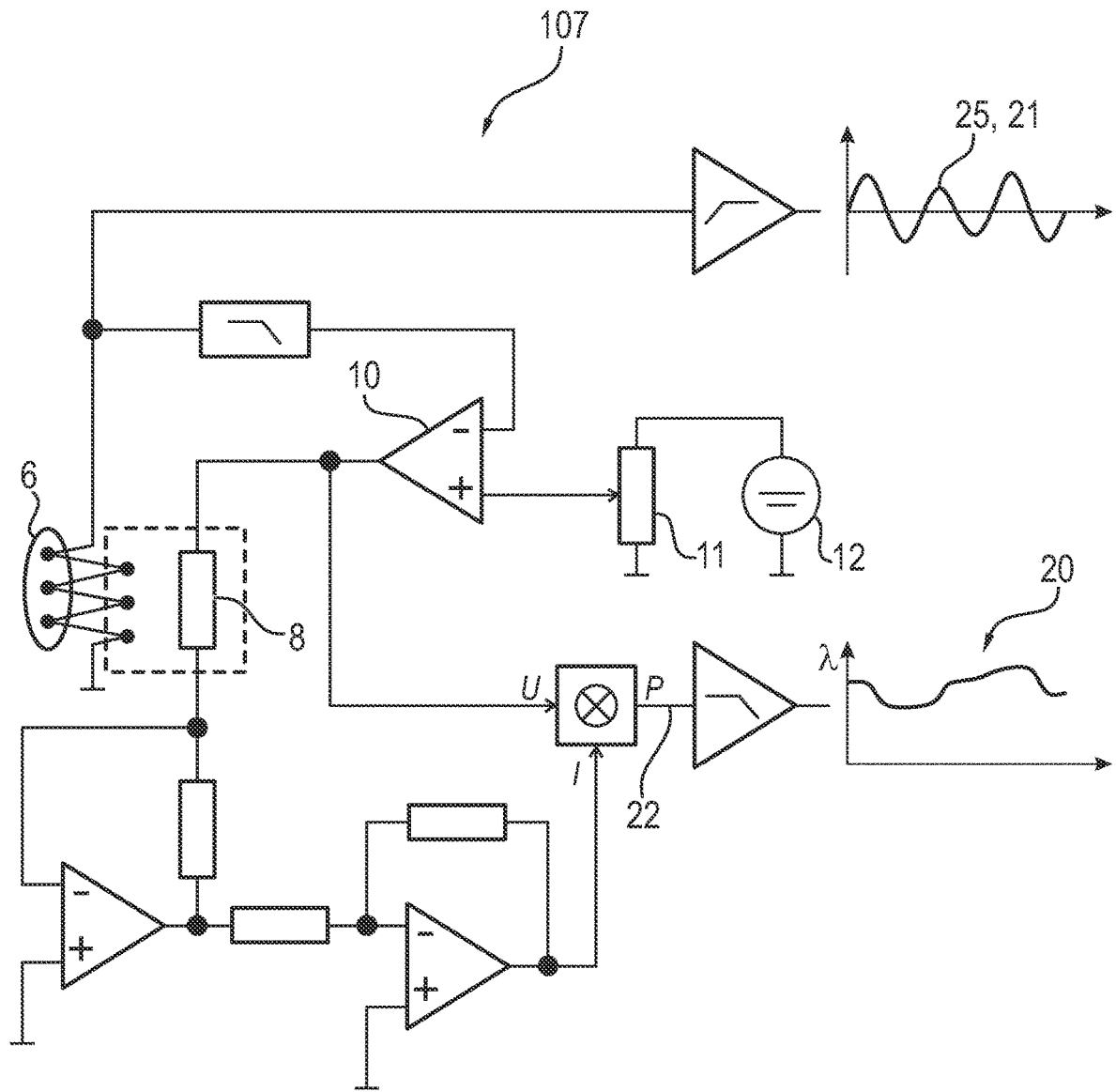
FIG. 3g is a schematic view showing a variant of an electronic circuit in which the heating power is used as a heat conduction signal.
Figure 3H:
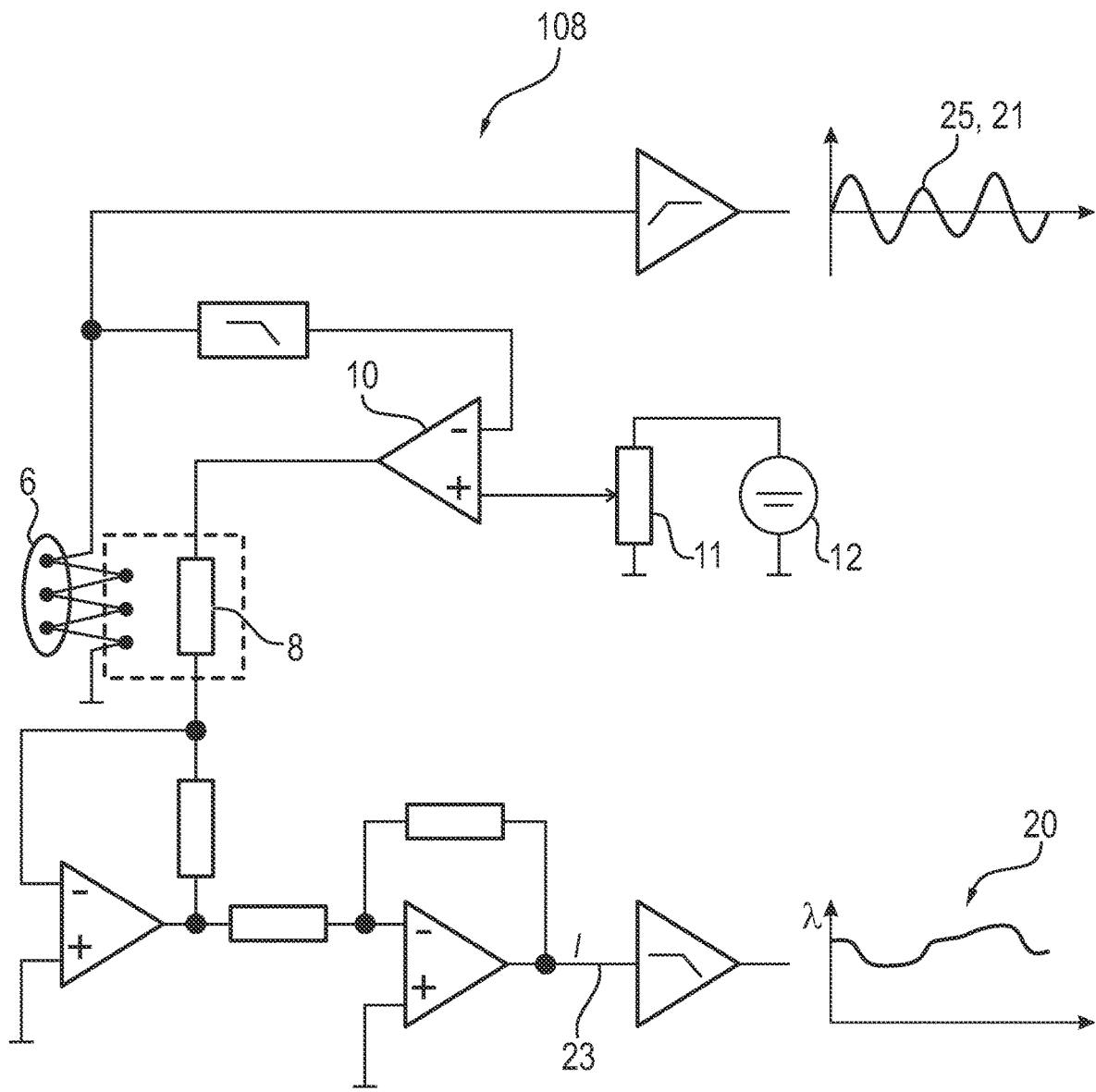
FIG. 3h is a schematic view showing a variant of an electronic circuit in which the heating current is used as a heat conduction signal.
Figure 3I:
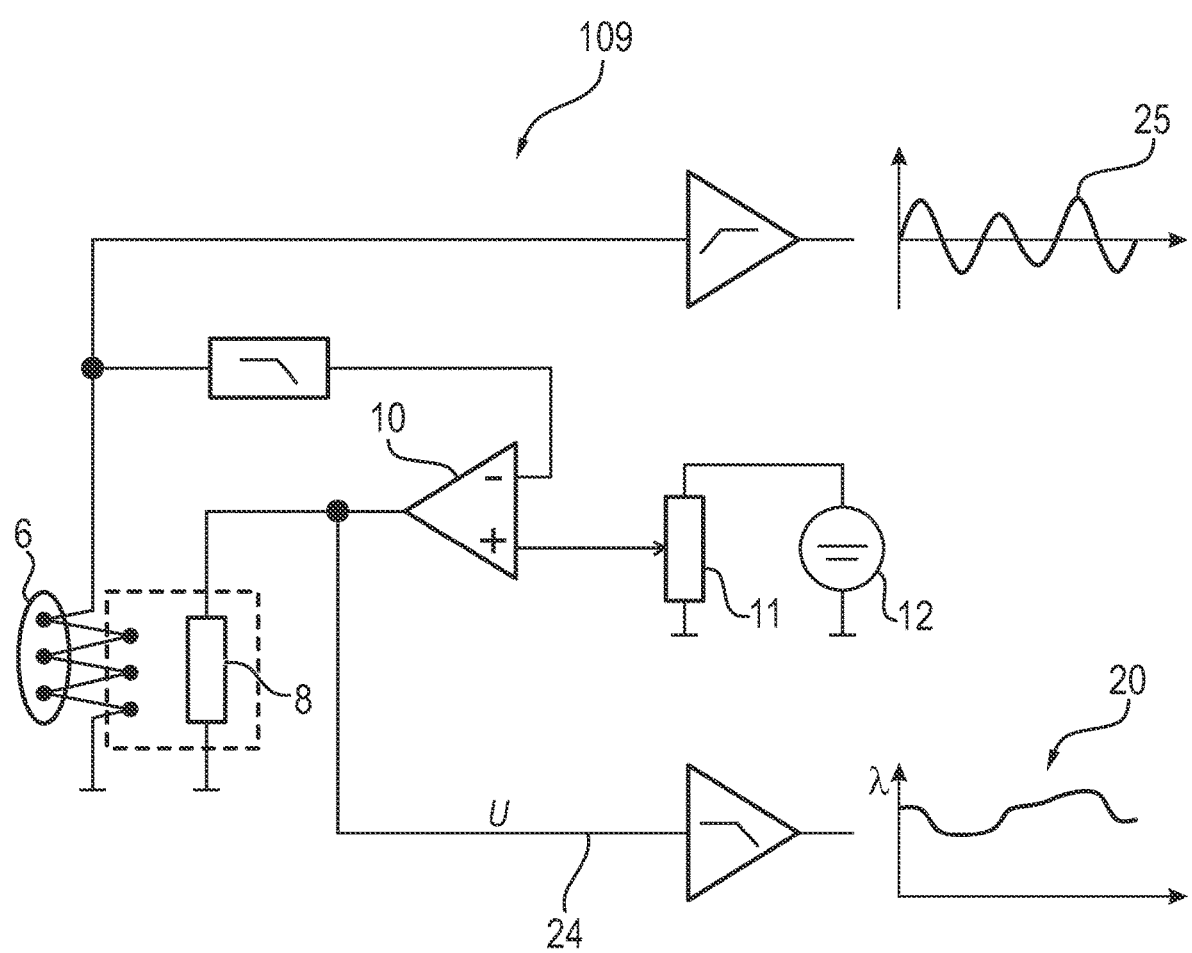
FIG. 3i is a schematic view showing a variant of an electronic circuit in which the heating voltage is used as a heat conduction signal.

The circuit configuration 102 of FIG. 3b, constant current control, differs from the configuration of FIG. 3a only in that the amplifier 10 is connected as a non-inverting amplifier, a portion of the output voltage of the amplifier being fed back to the inverting input of the amplifier through a voltage divider consisting of heater structure 8 and shunt 15. In the constant power control circuit 103 of FIG. 3c, the output (voltage) of the amplifier 10 connected to the first contact of the heating structure 8 is coupled to the first input of a multiplier 16, the second input (current) of which is connected to the second contact of the heating structure 8 via an inverting amplifier 17 and two series resistors. The output of the multiplier 16 is coupled to the inverting input of the amplifier 10. In the constant temperature control circuit 104 of FIG. 3d, the output (voltage) of the amplifier 10 connected to the first contact of the heating structure 8 is coupled to the first input of a multiplier 16, the second input (current) of which is connected to the second contact of the heating structure 8 via an inverting amplifier 17 and two series resistors. The output of the multiplier 16 is coupled to the low pass arrangement 13 and the high pass arrangement 14, which provide the DC and AC output signals. As shown in FIGS. 3d, 3e and 3f, during actuation the respective thermal operating points are controlled by circuit arrangements 104, 105, 106 to constant values independent of the gas composition. In this case, the output voltages of the heat conduction measuring unit 6 are used as controlled variables and heating voltages, heating currents, or heating powers are tracked. In this case, the carriers of the measured values are the required heating voltages 24, heating currents 23 and heating powers 22, respectively. FIGS. 3g, 3h, 3i show further possibilities of control with circuit arrangements 107, 108, 109, which represent combinations and variations of the aforementioned processes and circuit arrangements 101, 102, 103, 104, 105, 106 and combine the advantages of operation at constant temperature levels with comparatively simple (because slow) temperature control. Here, the output voltage of the heat conduction measuring unit 6 is used as the control variables, and the heating voltage, heating current, or heating power are tracked in such a way that the working temperatures are constant as a time average. The constant temperature averages produce stable measuring conditions, independent of the type of gas mixture, while the rapidly changing, modulation-related signals 25 (oxygen) remain directly measurable as temperature fluctuations without causing significant operating point shifts due to their lower amplitude. The control signals are conditioned using electronic low-pass arrangements in such a way that the temperature changes caused by the gas mixture (which are slower) are compensated without disturbing the faster periodic thermal conductivity changes (oxygen measured values) caused by the magnetic field.

Figure 4:
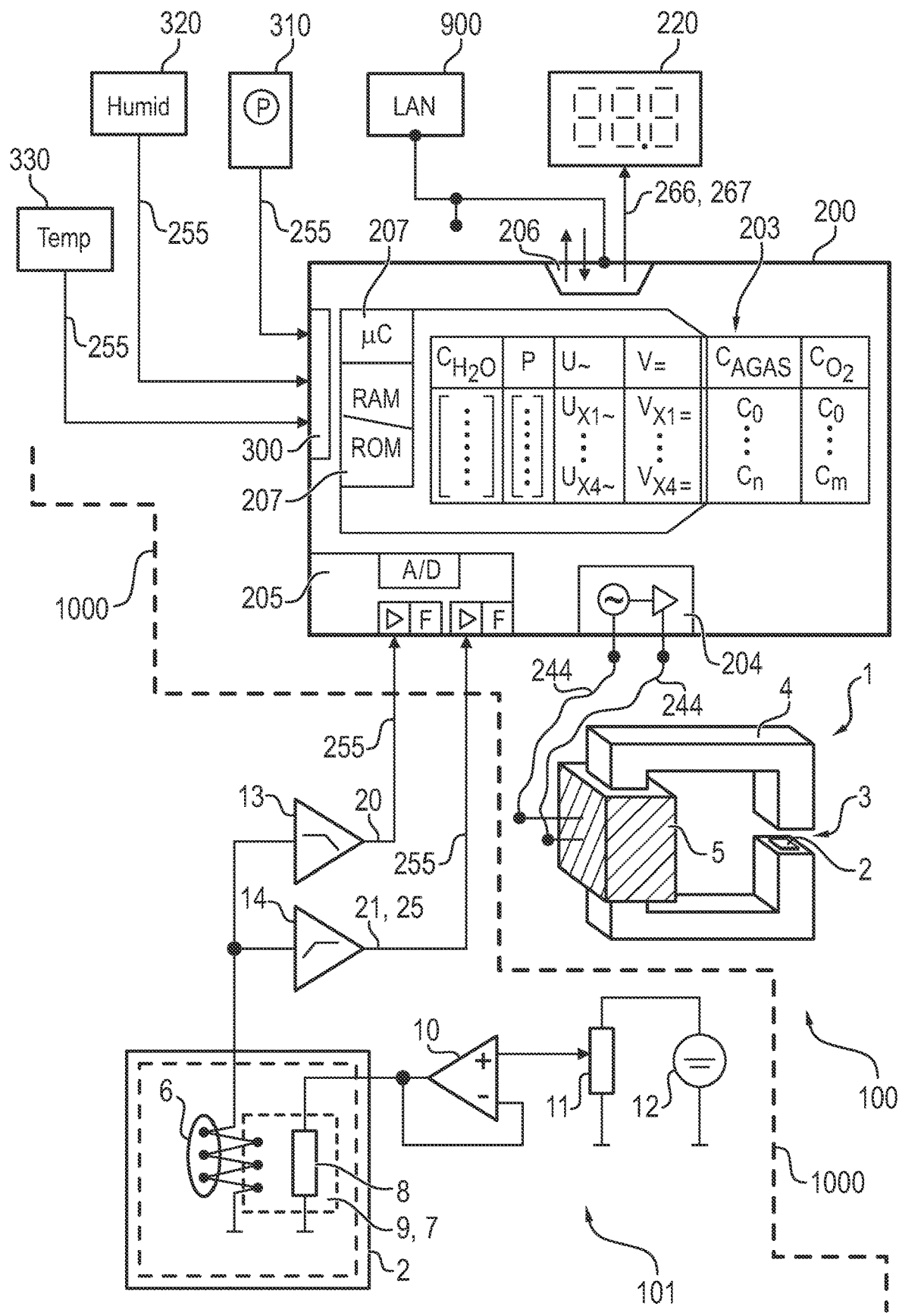
FIG. 4 is a schematic view showing a variant of the electronic circuit according to FIG. 3a with further components for operating the measuring device according to FIG. 1 and FIG. 2 with elements for signal evaluation, calculation and for determining the concentration.

In FIG. 4, the circuit arrangement 101 according to FIG. 3a is included as an example in an embodiment of the measuring device 1 to form a measuring system 100 which is suitably configured for determining a concentration of oxygen in a respiratory gas mixture and at least one further gas, in particular a volatile anesthetic gas. Identical elements in FIGS. 1, 2, 3a, 3b, 3c, 3d, 3f, 3g 3h, 3i and in FIG. 4 are designated by the same reference numerals in FIGS. 1, 2, 3a, 3b, 3c, 3d, 3f, 3g 3h, 3i and in FIG. 4. A dashed demarcation line graphically separates the components known from FIG. 3a from other components. A calculation and control unit 200 is provided, in particular in the form of a multifunctional calculation and control unit 200, which can also have, in addition to a calculation module 207 with data memory 207 (RAM, ROM), further modules, such as magnetic field control 204, signal processing 205 with amplifier elements, filter circuits and analogue-to-digital converters and also a data interface 206. The calculation and control unit 200 is configured for measured value and signal acquisition 310, 320, 255, 20, 21, 25, with a sensor measuring unit 300 or is connected to a sensor measuring unit 300.

Figure 5:
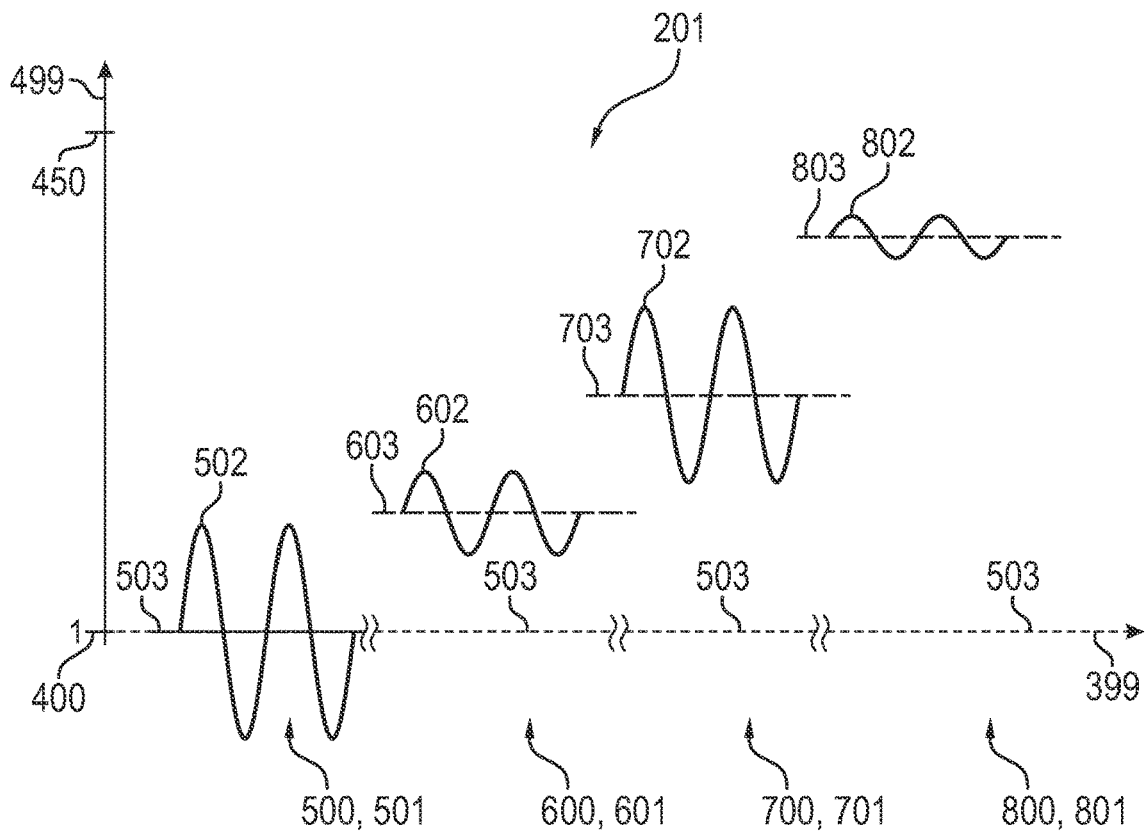
FIG. 5 is a view showing diagrams of thermo-voltage signals with DC voltage signal components and AC voltage signal components.
Figure 5:
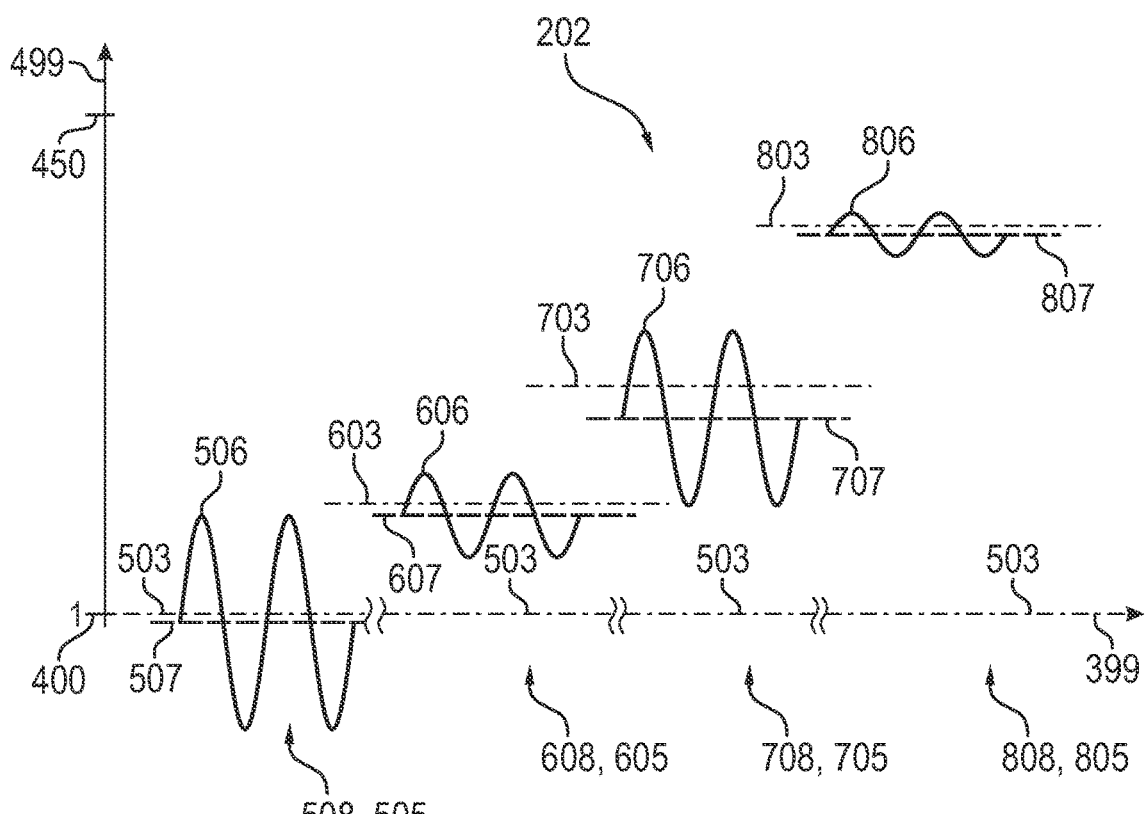

The calculation and control unit 200 may include a magnetic field controller 204, which is responsible for driving the electromagnet 4 via control lines 244 and thus for generating a magnetic field as an alternating magnetic field with an excitation frequency if in the range of 1 Hz to 100 Hz. Exemplary excitation frequencies are about 7 Hz or even 15 Hz. The measured value of the heat conduction measuring unit 6 is passed for evaluation via a low-pass arrangement 13 and via a high-pass arrangement 14. An AC signal component 21 is provided at the output of the high-pass arrangement 14. At the output of the low-pass arrangement 13 a DC signal component 20 is provided. The AC signal component 21 in the measured value represents an oxygen concentration in the gas composition of the gas sample. The DC voltage signal component 20 in the measured value represents a thermal conductivity of the gas composition of the gas sample. The calculation and control unit 200 receives from the circuit arrangement 101 according to FIG. 1a,—or also from the circuit arrangements 101, 102, 103, 104, 105, 106, 107, 108, 109 (FIGS. 3a-3i) by means of signal lines 255 the direct voltage signal component $U_{X=}$ 20 and the alternating voltage signal component $U_{X\sim}$ 21 for further data processing. In the measuring signals of the measuring element 2, or of the heat conduction measuring unit 6, twice the frequency 2f of the excitation frequency can be seen as the AC voltage signal component 21. This can be explained by the fact that the alignment of the oxygen molecules in the magnetic field, which reduces a degree of freedom of the mobility of the oxygen molecules in the gas mixture of the gas sample, is independent of the polarity of the excitation of the magnetic field and in this respect the alignment of the oxygen molecules during a period 1T of the excitation frequency if is twofold, i.e. with the frequency 2f. i.e. with the frequency 2f and then also becomes visible in the alternating voltage signal components $U_{X1\sim}$ 502, $U_{X2\sim}$ 602, $U_{X3\sim}$ 702, $U_{X4\sim}$ 802, $U_{X1F\sim}$ 506, $U_{X2F\sim}$ 606, $U_{X3F\sim}$ 706, $U_{X4F\sim}$ 806 (FIG. 5) of the thermoelectric voltage signals in the diagrams 201, 202 (FIG. 5).

The calculation and control unit 200 performs a standardization of the DC voltage signal components 20 and AC voltage signal components 21. This standardization of the signal components 20, 21 is carried out by the calculation and control unit 200 to a reference value 400. The reference value 400 is assumed to be a measured value of the thermoelectric voltage signals (FIG. 5) for a state in which a dry gas mixture with a gas concentration of 100% oxygen is supplied to the measuring device 1 with the gas sample and thus the measuring element 2 is also surrounded by a gas concentration of 100% oxygen.

For dry gas mixtures X1 500, X2 600, X3 700, X4 800 (FIG. 5) this results in standardized voltage signals with standardized alternating voltage signal components $U_{Y\sim}$ and standardized direct voltage signal components $U_{Y=}$. For humid gas mixtures X1F 508, X2F 608, X3F 708, X4F 808 (FIG. 5) this results in standardized voltage signals with standardized alternating voltage signal components $U_{YF\sim}$ and standardized direct voltage signal components $U_{YF=}$. The calculation and control unit 200 is configured to pressure compensate the standardized AC signal components $U_{Y\sim}$, $U_{YF\sim}$ into pressure compensated standardized AC signal components $U_{Z\sim}$, $U_{ZF\sim}$. The calculation and control unit 200 is configured to determine an oxygen concentration in the gas sample based on the standardized AC signal components $U_{Y\sim}$, $U_{YF\sim}$, $U_{Z\sim}$, $U_{ZF\sim}$.

The calculation and control unit 200 is configured to determine a concentration of another gas in the gas sample based on the standardized DC signal components $U_{Y=}$, $U_{YF=}$.

Information or data regarding moisture in the gas sample may be provided to the calculation and control unit 200 via the data interface 206 or by means of a moisture sensor 320 connected to the calculation and control unit 200 or connected to the measurement system 100 via signal lines 255. The moisture sensor 320 is in metrological contact with the gas mixture of the gas sample.

Information or data about the temperature in the gas sample may be provided to the calculation and control unit 200 via the data interface 206 or by means of a temperature sensor 330 connected to the calculation and control unit 200 or connected to the measurement system 100 via signal lines 255. The temperature sensor 330 is in metrological contact with the gas mixture of the gas sample.

Information or data on the pressure level of the gas sample may be provided to the calculation and control unit 200 via the data interface 206 or by means of a pressure sensor 310 connected to the calculation and control unit 200 or connected to the measurement system 100 via signal lines 255. The pressure sensor 310 is in a metrological contact with the gas mixture of the gas sample.

In the data memory 207 of the computing module 207, both in embodiments as volatile (RAM) or non-volatile (ROM) memory modules and in embodiments in the form of data carriers (hard disks, memory cards), data records 203 are stored in the form of tables or multi-dimensional data fields, on the basis of which it is possible for the calculation and control unit 200 to determine an oxygen concentration in the gas mixture of the gas sample by processing the alternating voltage signal components $U_{X\sim}$, $U_{XF\sim}$. In addition, it is possible for the calculation and control unit 200 to determine a concentration of a further gas in the gas mixture of the gas sample, preferably a concentration of a volatile anesthetic gas, such as desflurane, on the basis of the data sets 203 stored in the form of tables or multi-dimensional data fields and processing of the DC signal components $U_{X=}$, $U_{XF=}$. Anesthetic gases whose concentration can be determined based on the data and from the DC signal components by the calculation and control unit 200 are, for example, halothane, sevoflurane, enflurane, isoflurane or desflurane. The data records (data sets) 203, which are stored in the form of data fields or tables in the data memory 207, comprise information or correlations on signal characteristics which result for the DC signal components $U_{X=}$, $U_{XF=}$ under a wide variety of conditions with respect to the content of moisture, the pressure level and the temperature level. The data records 203, which are stored in the form of data fields or tables in the data memory 207, comprise information or correlations on signal characteristics which result for the AC voltage signal components $U_{X\sim}$, $U_{XF\sim}$ under a wide variety of conditions with regard to the moisture content, the pressure level and the temperature level. The information or correlations can be stored, for example, in the form of a table with measured values or pairs of values standardized to a dry gas mixture with a content of 100% oxygen, which were determined, for example, in a series of measurements with precise adjustment of the concentrations of oxygen, nitrogen and an anesthetic gas in the gas mixture. For example, the following concentration ranges of oxygen, nitrogen and at least one anesthetic gas may have been applied (data in % by volume):

Oxygen: 15%-100%,
Nitrogen: 0%-85%,
Anesthetic gas desflurane: 0%-20%,
Anesthetic gas isoflurane: 0%-12%,
Anesthetic gas sevoflurane: 0%-12%,
Anesthetic gas halothane: 0%-12%, Anesthetic gas enflurane: 0%-12%, Moisture range of the sample gas: 0%-95%, ATPS (Ambient Temperature Pressure Saturated).

Typical and common environmental conditions during implementation include:

Ambient pressure range: 400 hPa-1100 hPa,

Temperature range of the temperature-controlled measuring system: 55° C.-65° C., Ambient temperature range 10° C.-50° C.

This information or values may be stored as discrete data values in the data memory 207, the calculation and control unit 200 is configured in such a case, in the signal acquisition of the AC voltage signal components $U_{X1\sim}$ 502, $U_{X2\sim}$ 602, $U_{X3\sim}$ 702, $U_{X4\sim}$ 802, $U_{X1F\sim}$ 506, $U_{X2F\sim}$ 606, $U_{X3F\sim}$ 706, $U_{X4F\sim}$ 806 (FIG. 5) and DC voltage signal components $U_{X1=}$ 503, $U_{X2=}$ 603, $U_{X3=}$ 703, $U_{X4=}$ 803, $U_{X1F=}$ 507, $U_{X2F=}$ 607, $U_{X3F=}$ 707, $U_{X4F=}$ 807 (FIG. 5) occurring during operation of the measuring system 100 by interpolation, for example via an at least section-wise linear, quadratic, cubic, polynomial or spline interpolation, in order to map the assignment relationship more finely or at a finer level.

The information or correlations can alternatively or partially also be formed with the aid of calculation formulas determined from the measurement data, for example in the form of functions, similar to those shown in general form in the formulas 1 to 5 listed below. The functions can thereby represent, for example, as polynomial functions, in each case ranges of the concentration ranges of oxygen, nitrogen and at least one anesthetic gas under the influence of temperature, pressure level and moisture. The correlations in the data sets 203 (FIG. 4) can also include special features, such as signals superimposed on the signals 20, 21 (FIG. 4) or offset voltages of the electronic components (amplifiers, A/D converters, filter circuits) caused by the operation of the measuring device 1 (FIG. 4) and/or the measuring system 100 (FIG. 4) using the circuit arrangements 101, 102, 103, 104, 105, 106, 107, 108, 109 (FIGS. 3c to 3i). In this context, such correlations of assignment can also include the effects which act in the measuring device 1 on the heat balance at the measuring element 2 and the diaphragm 7 and thus also have an effect on the AC voltage signal components $U_{X1\sim}$ 502, $U_{X2\sim}$ 602, $U_{X3\sim}$ 702, $U_{X4\sim}$ 802, $U_{X1F\sim}$ 506, $U_{X2F\sim}$ 606, $U_{X3F\sim}$ 706, $U_{X4F\sim}$ 806 (FIG. 5) and direct voltage signal components $U_{X1=}$ 503, $U_{X2=}$ 603, $U_{X3=}$ 703, $U_{X4=}$ 803, $U_{X1F=}$ 507, $U_{X2F=}$ 607, $U_{X3F=}$ 707, $U_{X4F=}$ 807 (FIG. 5) during operation of the measuring system 100. In particular, effects can also be included in the assignment correlations 203 (FIG. 4) or data sets 203 (FIG. 4) that are due to the difference in the configurations of the circuit arrangements 101, 102, 103, 104, 105, 106, 107, 108, 109 (FIGS. 3c to 3i) with regard to the operation with temperature control of the measuring element 2 (FIG. 1, FIG. 2, FIG. 4, FIGS. 3c to 3i) and the type of control with open-loop and/or closed-loop control of the temperature control of the measuring element 2 (FIG. 1, FIG. 2, FIG. 4, FIGS. 3c to 3i) are conditioned, such as the operation with constant temperature of the heating structure, constant electric power, constant electric voltage, constant electric current by the circuit arrangements 101, 102, 103, 104, 105, 106, 107, 108, 109 (FIGS. 3c to 3i). The calculation and control unit 200 is further adapted to include in the determination of the oxygen concentration and/or in the determination of the further gas concentration, measured values of the pressure sensor 310 indicating a pressure level in the gas mixture of the gas sample and/or information provided by means of the data interface 206 regarding a pressure level in the gas mixture of the gas sample. The calculation and control unit 200 is further configured to include in the determination of the oxygen concentration and/or in the determination of the further gas concentration, measured values of the moisture sensor 320, which indicates a moisture situation in the gas mixture of the gas sample and/or information provided by means of the data interface 206 regarding a moisture in the gas mixture of the gas sample. The calculation and control unit 200 may further be configured to include, in the determination of the oxygen concentration and/or in the determination of the further gas concentration, measured values of the temperature sensor 330 which indicates a temperature level in the gas mixture of the gas sample and/or information provided by means of the data interface 206 regarding a temperature level in the gas mixture of the gas sample. The calculation and control unit 200 is further configured to include, when standardizing the measurement signals $U_{X=20}$, $U_{X\sim}$ 21 into standardized AC signal components $U_{Y\sim}$, $U_{YF\sim}$ and DC signal components $U_{Y=}$, $U_{YF=}$, measured values of the moisture sensor 320, measured values of the pressure sensor 310, measured values of the temperature sensor 330 and/or information provided by means of the data interface 206 regarding temperature, pressure level or moisture in the gas mixture of the gas sample. In the following, a process for operating the measuring system 100 for a determination of gas concentrations in a gas mixture of a gas sample is described on the basis of FIG. 4—partly with reference to FIG. 5. The process allows the determination of an oxygen concentration and an anesthetic gas concentration. The calculation and control unit 200—or another unit suitable for carrying out a process for the determination of the gas concentration of the further gas and the determination of the oxygen concentration of the measuring system 100 after the provision of the thermoelectric voltage signals 20, 21 by the heat conduction measuring unit 6 on the measuring element 2 and signal processing 205, the following process steps are carried out by the computing module 207 and further components 13, 14, 205 of the measuring system 100:

a. Signal Separation:

A separation (AC← →DC-separation) of the thermo-voltage signals into a DC-signal component (DC-component) 20 and an AC-signal component (2f-component) 21 takes place. Since the AC signal component (2f component) 21 is several orders of magnitude smaller than the DC signal component 20, this 2f component 21 must be amplified to a correspondingly significantly higher level than the DC signal component 20 prior to the subsequent analog-to-digital conversion 205. Such signal amplification of the AC signal components 21 can typically be performed with an amplification factor in the range of 20 to 750. The amplitude of the 2f signal is determined by the calculation and control unit 200 and calculation module 207, for example in a digital manner, using a lock-in process. Prior to separation (AC← →DC-separation) of the thermo-voltage signals into a DC-signal portion (DC-portion) 20 and an AC-signal portion (2f-portion) 21, a signal amplification of the thermo-voltage signals (DC- and AC-signal portion) may be provided. Such signal amplification can typically be performed with an amplification factor in the range of 5 to 20. Overall, the amplification of the AC voltage signal components 21 then results in a typical amplification value above 200.

b. Moisture Compensation:

In an optional manner, a compensation of the alternating voltage signal components (2f-component) 21 and/or of the direct voltage signal components 20 can take place, so that signals 20', 21' (FIG. 7) with a DC-component and a 2f-component result, as they would have been recorded without a water vapor component—i.e. for a dry gas mixture, so that values result which correspond to dry gas. For this purpose, measured values of the moisture sensor 320 or information indicating a moisture content in the gas mixture of the gas sample are used.

c. Standardization/Calibration:
  i. Standardization of the AC signal components:
    The AC signal component 21 is standardized to a reference signal 502 (FIG. 5), which corresponds to an AC signal component without any influence of moisture or moisture content in the gas mixture of the gas sample with a volume content of 100% oxygen. This reference signal 502 has previously been obtained by means of measurement experiments.
    This results in standardized alternating voltage signal components $U_{Y\sim}$, $U_{YF\sim}$.
  ii. Standardization of the DC voltage signal components:
    The DC voltage signal component 20 is standardized to a reference signal 503, 400 (FIG. 5), which corresponds to a DC voltage signal component without a moisture influence or proportion of moisture in the gas mixture of the gas sample with a volume proportion of 100% oxygen. This reference signal 503, 400 has previously been obtained by means of measurement experiments.
    This results in standardized DC voltage signal components $U_{Y=}$, $U_{YF=}$.

d. Pressure Compensation:
  Pressure compensation of the standardized alternating voltage signal components $U_{Y\sim}$, $U_{YF\sim}$ takes place so that pressure-compensated, standardized signals $U_{Z\sim}$, $U_{ZF\sim}$ with a 2f component result, as they would have been recorded at a reference pressure of, for example, 1013 hPa for a dry gas mixture, so that a value results which corresponds to dry gas at standard pressure. For this purpose, measured values of the pressure sensor 310 or information indicating the current pressure level in the gas mixture of the gas sample are used.

e. Calculation of the Oxygen Concentration.
  The pressure-compensated standardized AC signal components $U_{Z\sim}$, $U_{ZF\sim}$ are used to determine the oxygen concentration in the gas mixture of the gas concentration and to determine therefrom an output signal which indicates the oxygen concentration in the gas mixture of the gas concentration.

f. Calculation of the Concentration of the Further Gas in the Gas Mixture of the Gas
  concentration, in particular an anesthetic gas concentration in the gas mixture of the gas concentration. The standardized DC signal components $U_{Y=}$, $U_{Y=}$ are used to determine the concentration of the further gas, in particular the anesthetic gas concentration, and to determine therefrom an output signal which indicates the concentration of the further gas, in particular the anesthetic gas concentration, in the gas mixture.

The described steps a)-f) can also be carried out in a varied sequence of steps in the sense of the present invention, for example the sequence of standardization and compensation of pressure, or moisture can be carried out in a different order, depending on the preparation and design of the data sets 203 and reference signals 400, 502, 503, which have been obtained beforehand with the aid of measurement experiments.

In one of the steps of the process or in a further step, for example in one of steps b), c) or d), an adjustment of the heat-conducting and heat-dissipating properties of the measuring element may be carried out. Such an adjustment with respect to the differences between different measuring elements due to the series dispersion of the measuring elements with respect to the heat-conducting and heat-dissipating properties may be performed, for example, as outlined below:
  Test gas supply and operation of the measuring element at the standard operating point
  Acquisition of the DC voltage signal components $U_{X=}$, $U_{X\sim}$,
  optional repetition of the previous steps with other gases
  Comparisons of the signal components with standard values or with reference values
  Determination of correction values In one of the steps of the process or in a further step, preferably in step d), a pressure compensation of the DC signal components $U_{X=}$ or of the standardized DC signal components $U_{Y=}$ can be carried out. The pressure compensation makes it possible to compensate for differences in the density and thus in the thermal conductivity of the gas mixture of the gas sample. Differences in density arise, for example, in the case of an application at high altitudes, such as altitudes of more than 2500 meters, for example, in mountains or in aircraft.

In one of the steps of the process or in a further step, preferably in one of the steps b) or c), a temperature compensation of the DC voltage signal components can be performed. In one of the steps of the process or in a further step, preferably in one of the steps b) or c), a temperature compensation of the AC voltage signal components can be performed.

In one of the steps of the process or in a further step, preferably in one of the steps b) or c), a moisture compensation of the DC signal components can be performed. In one of the steps of the process or in a further step, preferably in one of the steps b) or c), a moisture compensation of the AC voltage signal components can be performed.

The calculation and control unit 200 may provide output signals 266, 267 based on the determined gas concentration of the further gas concentration and/or the determined oxygen concentration in the gas mixture of the gas sample, which comprises and/or indexes the oxygen concentration and the concentration of at least one further gas. The output signal 266, 267 may be used to provide a numeric, alpha-numeric or a graphical output on an output unit 220 to inform a user of the results of the gas concentration measurement. The output signal 266, 267 may also be used to provide the determined gas concentration of the further gas concentration and/or the determined oxygen concentration in the gas mixture of the gas sample to a data network 900 via the data interface 206. In an optional embodiment, the data interface 206 may also be bidirectional to provide externally provided information from the data network 900 to the calculation and control unit 200. Such externally provided information may include, for example, information regarding a dosing state of a dosing (metering) system configured to dose the further gas, for example desflurane and/or to dose oxygen. Such a dosing system may be a dosing device for gases with a valve arrangement or an anesthetic vaporizer (vapor) for a dosage of volatile anesthetics (desflurane, halothane, sevoflurane, enflurane, isoflurane). Such externally provided information may also include information regarding a gas composition of the gas mixture of the gas sample, which is for example acquired and provided by another external system, for example by an anesthetic gas monitor for a determination of anesthetic gases in a gas mixture.

FIG. 5 shows diagrams 201, 202. With assignment to an ordinate (x-axis) 399, voltage signals are plotted in the diagrams 201, 202 on the abscissa (y-axis) 499 for four different gas compositions 500, 600, 700, 800, respectively, by way of example. Identical elements in FIGS. 1, 2, 3a, 3b, 3c, 3d, 3f, 3g 3h, 3i, 4 and in FIG. 5 are designated by the same reference numerals in FIGS. 1, 2, 3a, 3b, 3c, 3d, 3f, 3g 3h, 3i, 4 and FIG. 5. In diagram 201 the thermoelectric voltage signals $U_{X1}$ 501, $U_{X2}$ 601, $U_{X3}$ 701, $U_{X4}$ 801 resulting at the measuring element 2 (FIG. 1, FIG. 2, FIG. 4) as output signals of the measuring elements 2 (FIG. 2) according to the embodiments of the measuring device 1 as measuring system 100 according to FIG. 4, are shown standardized for the four exemplary gas compositions X1 500, X2 600, X3 700, X4 800 without an influence of moisture in the gas sample. In diagram 202 the thermoelectric voltage signals $U_{X1F}$ 505, $U_{X2F}$ 605, $U_{X3F}$ 705, $U_{X4F}$ 805 resulting at the measuring element 2 (FIG. 1, FIG. 2, FIG. 4) as output signals of the measuring elements 2 (FIG. 2) according to the configurations of the measuring device 1 as measuring system 100 according to FIG. 4 are shown standardized for four further exemplary gas compositions X1F 508, X2F 608, X3F 708, X4F 808 under the influence of moisture in the gas sample.

The signal characteristics of the thermoelectric voltage signals $U_{X1}$ 501, $U_{X2}$ 601, $U_{X3}$ 701, $U_{X4}$ 801 in diagram 201 and $U_{X1F}$ 505, $U_{X2F}$ 605, $U_{X3F}$ 705, $U_{X4F}$ 805 in diagram 202 were recorded in the measurement test under usual ambient conditions of ambient temperature, temperature of the gas mixture of the gas sample and air pressure. One can assume a temperature range of approximately 12° C. to 28° C. for the ambient temperature and the temperature of the gas mixture of the gas sample and a pressure range of approximately 1000 hPa to 1025 hPa. The standardization is based on the thermoelectric voltage signal $U_{X3}$ 503, 400 which is the output signal of a heated measuring element 2, 8 (FIG. 1, FIG. 2) when a dry gas mixture with a gas concentration of 100% oxygen is supplied to the measuring device 1 (FIG. 1; FIG. 2) and thus the measuring element 2 (FIG. 1; FIG. 2) is also surrounded by a gas concentration of 100% oxygen.

The four exemplary gas compositions 500, 600, 700, 800 are composed as follows, as different compositions of air, or oxygen with an exemplary selected volatile anesthetic gas—in the embodiments of this FIG. 5, the agent sevoflurane is selected for this purpose:

Gas composition X1 500: 100% oxygen,
Gas composition X2 600: 100% air (oxygen content 21%),
Gas composition X3 700: 97% oxygen, 3% sevoflurane,
Gas composition X4 800: 97% air, 3% sevoflurane.

For these four gas compositions X1 500, X2 600, X3 700, X4 800, the time courses of standardized thermoelectric voltage signals $U_{X1}$ 501, $U_{X2}$ 601, $U_{X3}$ 701, $U_{X4}$ 801 are assigned and displayed on the abscissa 499. Thereby for each gas composition X1 500, X2 600, X3 700, X4 800 in each case a direct voltage signal component and an associated superimposed sinusoidal alternating voltage signal component are shown in the time courses of the standardized thermoelectric voltage signals $U_{X1}$ 501, $U_{X2}$ 601, $U_{X3}$ 701, $U_{X4}$ 801. The separation of DC voltage components and AC voltage components can be achieved—as shown in FIG. 4 in the measuring system 100 (FIG. 4)—by using suitable signal filtering with low-pass arrangements 13 (FIG. 1) and high-pass arrangements 14 (FIG. 4), respectively, in such a way that DC voltage signal components and AC voltage signal components result for the different gas compositions. These DC and AC voltage signal components are provided by the measuring device 1 (FIG. 1, FIG. 2, FIG. 4) for further evaluation with regard to the gas composition.

The further evaluation with regard to the gas composition can be carried out by means of a calculation and control unit 200 (FIG. 4) arranged in the measuring system 100 (FIG. 4). In this case, the thermoelectric voltage signals $U_{X1}$ 501, $U_{X2}$ 601, $U_{X3}$ 701, $U_{X4}$ 801 are evaluated with the direct voltage signal components and alternating voltage signal components previously standardized to 100% dry oxygen in such a way that the then resulting standardized periodic alternating voltage signal component and the non-periodic direct voltage signal component are related to each other and evaluated in order to determine an oxygen concentration in the gas sample of the gas mixture with high accuracy. With reference to the signal characteristics of the standardized thermoelectric voltage signals $U_{X1}$ 501, $U_{X2}$ 601, $U_{X3}$ 701, $U_{X4}$ 801, this means, for example, that the standardized alternating voltage signal components $U_{X1\sim}$ 502, $U_{X2\sim}$ 602, $U_{X3\sim}$ 702, $U_{X4\sim}$ 802 can be set in relation to the standardized direct voltage signal components $U_{X1=}$ 503, $U_{X2=}$ 603, $U_{X3=}$ 703, $U_{X4=}$ 803 and can be compared with one another and the oxygen concentration in the gas mixture of the gas sample can be determined from the ratio formed in this way or on the basis of the comparison.

In addition to the determination of the oxygen concentration in the gas sample of a gas mixture, a determination of a further gas concentration takes place within the scope of the evaluation by the calculation and control unit 200 (FIG. 4). Such a further gas concentration is, for example, the volatile anesthetic agent sevoflurane, the effects of which on the measured values have also been selected for illustration in the exemplary representations of the thermoelectric voltage signals $U_{X3}$ 701, $U_{X4}$ 801.

Measurement experiments have shown that the amplitude of the alternating voltage signal components $U_{X1\sim}$ 502, $U_{X2\sim}$ 602, $U_{X3\sim}$ 702, $U_{X4\sim}$ 802, under certain and known boundary conditions (magnetic field operating point) and taking into account or compensating for environmental influences (pressure, moisture) in gas mixtures of any gas mixtures of oxygen and air, or oxygen and nitrogen with a proportion of a volatile anesthetic agent, for example sevoflurane (3% in the alternating voltage signal components U 702, U 802) has an almost linear dependence. Oxygen and nitrogen with a proportion of a volatile anesthetic agent, for example sevoflurane (3% in the alternating voltage signal components $U_{X3\sim}$ 702, $U_{X4\sim}$ 802) has an almost linear dependence on the oxygen concentration in the gas mixture of the gas sample.

$$\hat{U}_{Xn\sim} = f(c_{O2}) \qquad \text{Formula 1}$$

In addition, the amplitude of the AC signal components $U_{X1\sim}$ 502, $U_{X2\sim}$ 602, $U_{X3\sim}$ 702, $U_{X4\sim}$ 802 is dependent on the proportion of the concentration of volatile anesthetic gas (AGas) as anesthetic agent, for example sevoflurane in the gas mixture of the gas sample.

$$\hat{U}_{Xn\sim} = f(c_{AGas}) \qquad \text{Formula 2}$$

$$\hat{U}_{Xn\sim} = f(c_{Sevofluran}) \qquad \text{Formula 2.1}$$

The level of the standardized DC signal components $U_{X1=}$ 503, $U_{X2=}$ 603, $U_{X3=}$ 703, $U_{X4=}$ 803 depends on the thermal conductivity of the gas mixture of the gas sample, i.e. on the proportional composition of oxygen, air, moisture, nitrogen, and volatile Anesthetic gas (AGas) as an anesthetic agent, for example sevoflurane in the gas mixture of the gas sample. The higher the concentration of volatile anesthetic agent in the gas mixture of the gas sample, the lower the total thermal conductivity of the gas mixture, and accordingly the DC signal component $U_{Xn=}$ standardized to a signal $U_{X1=}$ 503, 400 with a dry gas with 100% oxygen increases in relation to this standardization signal $U_{X1=}$ 503, 400.

$$U_{Xn=} = f(c_{AGas}, c_{Air}, c_{O2}, c_{cN2}, \text{Humidity}) \quad \text{Formula 4}$$

The lower the concentration of oxygen in the gas mixture of the gas sample, the lower the paramagnetic effect on the total thermal conductivity of the gas mixture, accordingly the amplitude of the AC signal component $\hat{U}_{Xn\sim}$ standardized to a signal $\hat{U}_{X1\sim}$ 502, 400 with a dry gas containing 100% oxygen decreases compared to this standardization signal $\hat{U}_{X1\sim}$ 502, 400.

$$\hat{U}_{Xn=} = f(c_{AGas}, c_{Air}, c_{O2}, c_{N2}, \text{Humidity}) \quad \text{Formula 5}$$

This is illustrated by the signal characteristics of the thermoelectric voltage signals $U_{X1}$ 501, $U_{X2}$ 601, $U_{X3}$ 701, $U_{X4}$ 801 in diagram 201 with the DC voltage signal components $U_{X1=}$ 503, $U_{X2=}$ 603, $U_{X3=}$ 703, $U_{X4=}$ 803 and the AC voltage signal components $U_{X1\sim}$ 502, $U_{X2\sim}$ 602, $U_{X3\sim}$ 702, $U_{X4\sim}$ 802. The influence of the moisture in the gas sample on the DC voltage signal component and the AC voltage signal component is exemplified in diagram 202 by the signal characteristics of the thermoelectric voltage signals $U_{X1F}$ 505, $U_{X2F}$ 605, $U_{X3F}$ 705, $U_{X4F}$ 805 with the DC voltage signal components $U_{X1F=}$ 507, $U_{X2F=}$ 607, $U_{X3F=}$ 707, $U_{X4F=}$ 807 and the AC voltage signal components $U_{X1F\sim}$ 506, $U_{X2F\sim}$ 606, $U_{X3F\sim}$ 706, $U$ 806$_{X4F\sim}$.

Since in the operation of the measuring device 1 (FIGS. 1, 2, 4) by means of the heating structure 8 (FIGS. 1, 2, 4) a supply and/or tracking of heating energy in the form of electrical energy for the measuring element 2 (FIGS. 1, 2, 4) on the membrane 7 (FIGS. 1, 2, 4) a constant electrical energy, electrical power, electrical voltage, electrical current or temperature, resp. excess temperature in relation to a reference temperature is set, i.e. adjusted, controlled or regulated, even in the event of changes in the gas composition in the gas sample—and thus resulting changes in the overall thermal conductivity of the gas mixture in this gas sample—the thermovoltage signals and changes in the thermovoltage signals represent a measure of changes in the setting and tracking of the heating energy which can be caused by changes in the thermal conductivity in the gas mixture of the gas sample.

Basically, physics shows that most liquids have higher thermal conductivities than gases or gas mixtures. If one considers thermal conductivities of different gases—in this diagram 201, for example, in a gas sample 500 of air ($\lambda$=0.02603 W/mK), or of essentially approximately 78% nitrogen in a mixture with 21% oxygen in comparison with a gas sample 600 of 100% oxygen ($\lambda$=0.02615 W/mK)—, an increase in the DC signal components $U_{X1=}$ 503, $U_{X2=}$ 603 can be seen with a decrease in the total thermal conductivity of the gas mixture in the gas sample. This can be explained by the fact that with a reduced thermal conductivity less electrical energy has to be supplied to the measuring element 2 (FIG. 4) as heating energy in order to set a certain defined temperature level on the measuring element 2, since due to a reduced thermal conductivity of the gas mixture less energy is carried away by the gas and transferred from the measuring element 2 (FIG. 4) to the gas mixture. An increase in the total thermal conductivity of the gas mixture, however, is accompanied by a decrease in the temperature on the measuring element 2 (FIG. 4) and, associated with this, a decrease in the thermoelectric voltage signals in the gas sample.

In Diagram 202, instead of the four exemplary dry gas compositions in Diagram 201, there are now shown four moist gas compositions X1F 508, X2F 608, X3F 708, X4F 808, which are composed as follows as different compositions of air, or oxygen with an exemplary selected volatile anesthetic gas—in the representations of this FIG. 5, the agent sevoflurane is selected—and a content of water vapor ($H_2O$) with 100% saturated vapor:

Gas composition X1F 508: 100% oxygen, 3% $H_2O$,
Gas composition X2F 608: 100% air (oxygen content 21%), 3% $H_2O$,
Gas composition X3F 708: 97% oxygen, 3% sevoflurane, 3% $H_2O$,
Gas composition X4F 808: 97% air, 3% sevoflurane, 3% $H_2O$.

The 100% saturated vapor of water ($H_2O$) corresponds—according to vapor pressure tables—in this diagram 202 to a gas concentration of approximately 3% $H_2O$ in the gas mixture of the gas sample at the temperature of 24° C. The influence of the moisture in the gas sample on the DC signal component and the AC signal component is shown in diagram 202 by the signal characteristics of the thermoelectric voltage signals $U_{X1F}$ 505, $U_{X2F}$ 605, $U_{X3F}$ 705, $U_{X4F}$ 805 with the DC voltage signal components $U_{X1F=}$ 507, $U_{X2F=}$ 607, $U_{X3F=}$ 707, $U_{X4F=}$ 807 and the AC voltage signal components $U_{X1F\sim}$ 506, $U_{X2F\sim}$ 606, $U_{X3F\sim}$ 706, $U_{X4F\sim}$ 806.

The voltage signals $U_{X1F}$ 505, $U_{X2F}$ 605, $U_{X3F}$ 705, $U_{X4F}$ 805 resulting at the measuring element 2 (FIG. 1, FIG. 2, FIG. 4) for four exemplary moist gas compositions 508, 608, 708, 808 are shown in diagram 202. The standardization is carried out on the thermoelectric voltage signal $U_{X1}$ 501, which is obtained as the time courses of the output signal of a heated measuring element 2, 8 (FIG. 1, FIG. 2), when a dry gas mixture with a gas concentration of 100% oxygen is supplied to the measuring device 100 (FIG. 1; FIG. 2) and thus the measuring element 2 is also surrounded by a gas concentration of 100% oxygen. In diagram 202, changes in the thermo-voltage signals $U_{X1F}$ 505, $U_{X2F}$ 605, $U_{X3F}$ 705, $U_{X4F}$ 805 under the influence of moisture are apparent. In particular, the DC voltage signal components $U_{X1F=}$ 507, $U_{X2F=}$ 607, $U_{X3F=}$ 707, $U_{X4F=}$ 807 are lower in the moist gas mixture of the gas sample than the DC voltage signal components $U_{X1=}$ 503, $U_{X2=}$ 603, $U_{X3=}$ 703, $U_{X4=}$ 803 in the dry gas mixture according to diagram 201, while the AC voltage signal components $U_{X1F\sim}$ 506, $U_{X2F\sim}$ 606, $U_{X3F\sim}$ 706, $U_{X4F\sim}$ 806 in this schematic representation according to diagrams 201, 202 do not differ significantly from one another within the scope of the measurement accuracies provided for this measurement test. Since for obtaining the thermo-voltage signals $U_{X1}$ 501, $U_{X2}$ 601, $U_{X3}$ 701, $U_{X4}$ 801 the measuring elements 2 (FIG. 2) have been operated for temperature control with a circuit arrangement 101 (FIG. 3a) with a substantially constant supply of energy, it can be concluded from such a reduction in the thermovoltage signals that the temperature of the measuring element 2 (FIG. 2) has reduced overall under the influence of moisture. This means that a portion of the constant energy supplied was conducted away from the measuring element 2 (FIG. 2) into the gas mixture and thus could not contribute to a temperature control of the measuring element 2 (FIG. 2). Water vapor forms—especially in the case of saturated vapor—molecular clusters in the gas mixture of the gas sample. The DC voltage signal components $U_{X1F=}$ 507, $U_{X2F=}$ 607, $U_{X3F=}$ 707, $U_{X4F=}$ 807 of the thermoelectric voltage signals decrease in comparison with dry gas mixtures in the case of a moist gas mixture, since part of the energy supplied is required to release the water vapor molecules from the molecular arrangement in the molecular clusters. As a result of this effect, in operation of the measuring system 100 (FIG. 4) under the influence of moisture, there is a reduction in the DC voltage signal components $U_{X1F=}$ 507, $U_{X2F=}$ 607, $U_{X3F=}$ 707, $U_{X4F=}$ 807 of the thermoelectric voltage signals, although on the basis of the thermal conductivity of water vapor ($\lambda$=0.0199 W/mK), a decrease in the total thermal conductivity of the gas mixture in the gas sample—and thus also an increase in the DC voltage signal components $U_{X1F=}$ 507, $U_{X2F=}$ 607, $U_{X3F=}$ 707, $U_{X4F=}$ 807 of the thermoelectric voltage signals—would be expected. From this it can be concluded that in this configuration of a resulting heat balance for the measuring element 2 (FIG. 4) with effects of heat flow, heat conduction, heat radiation, there is an increased energy requirement to release the water vapor molecules from the molecular clusters, than would result as expected from the reduction of the total thermal conductivity by the proportion of water vapor ($\lambda$=0.0199 W/mK) in the gas sample compared with the reference value 400, 503.

Since the measuring device 1 is essentially not a measuring device for determining thermal conductivities in gases, but a measuring device 1 for determining gas concentrations in gas mixtures by utilizing paramagnetism of certain gases, in particular oxygen in combination with thermal conductivity effects, which act on a state of the measuring element 2 (FIGS. 1, 2, 4) and on the operation of the measuring element 2 (FIGS. 1, 2, 4), the differences in the signal courses of the thermoelectric voltage signals $U_{X1F}$ 505, $U_{X2F}$ 605, $U_{X3F}$ 705, $U_{X4F}$ 805 with the DC voltage signal components $U_{X1F=}$ 507, $U_{X2F=}$ 607, $U_{X3F=}$ 707, $U_{X4F=}$ 807 and the AC voltage signal components $U_{X1F\sim}$ 506, $U_{X2F\sim}$ 606, $U_{X3F\sim}$ 706, $U_{X4F\sim}$ 806, which are associated with a moist gas mixture, to the signal characteristics $U_{X1}$ 501, $U_{X2}$ 601, $U_{X3}$ 701, $U_{X4}$ 801 in diagram 201 with the DC voltage signal components $U_{X1=}$ 503, $U_{X2=}$ 603, $U_{X3=}$ 703, $U_{X4=}$ 803 and the alternating voltage signal components $U_{X1\sim}$ 502, $U_{X2\sim}$ 602, $U_{X3\sim}$ 702, $U_{X4\sim}$ 802, which belong to a dry gas mixture, are based on a combination of different effects. These effects result from changes in the gas compositions with resulting changes in the thermal conductivity and the heat balance in the measuring device 1 (FIGS. 1, 2, 4) and their changes and effects on the heat balance at the measuring element 2 (FIG. 4). The heat balance at the measuring element 2 (FIG. 4) results during operation of the measuring system 100 (FIG. 4) from effects of heat transport, such as heat dissipation to the environment by thermal radiation, effects of heat flow (convection) into the gas sample, effects of heat dissipation by thermal conduction within the measuring device 1 or to the outside of the measuring device 1 (FIGS. 1, 2, 3, 4), effects of heat conduction within the membrane 7 (FIGS. 1, 2, 3, 4) and to the surrounding structures of the measuring device (FIG. 4), as well as effects caused by heat dissipation by heat conduction through the electrical contacting of the measuring device 1 (FIGS. 1, 2, 4).

Figure 6:
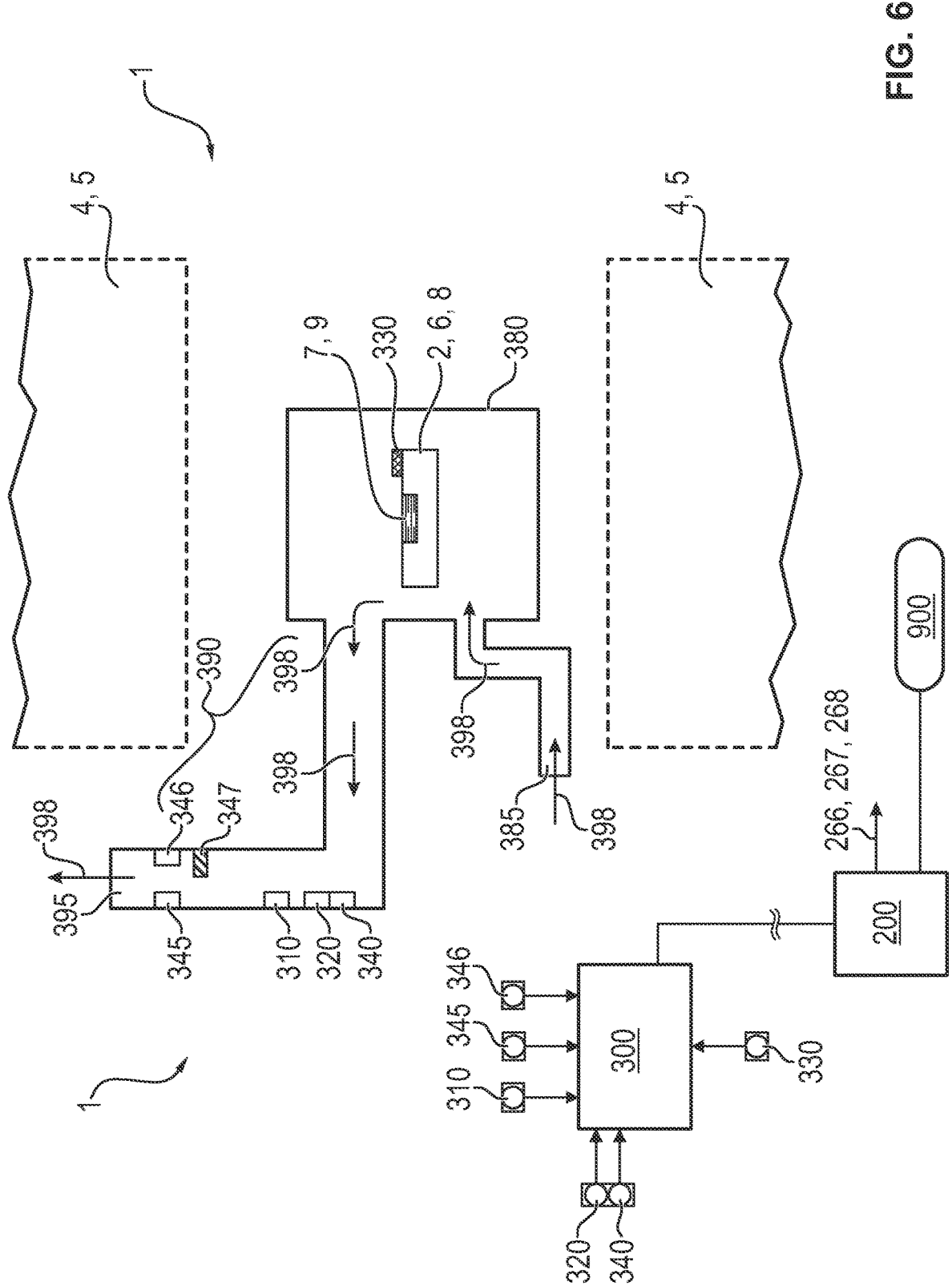
FIG. 6 is a schematic view showing how the measuring device can be supplemented with further sensor technology and how the measuring device is arranged in the measuring system with measuring chamber, purge chamber, gas guide, gas supply and gas outlet for gas flow, flowing over or around the measuring element.

FIG. 6 shows the measuring device 1 schematically integrated in a gas duct 398 with a pressure sensor 310, moisture sensor 320, temperature sensor 330, a further reference temperature sensor 340, a first thermistor 345, a second thermistor 346 with arrangement of measuring chamber 380, measuring element 2, purge chamber 390 in the measuring device 1 with gas supply 385 and gas outlet 395. Identical elements in FIGS. 1, 2, 3a, 3b, 3c, 3d, 3f, 3g 3h, 3i, 4, 5 and in FIG. 6 are designated with the same reference numerals in FIGS. 1, 2, 3a, 3b, 3c, 3d, 3f, 3g 3h, 3i, 4, 5 and FIG. 6. The measured values of the sensors 310, 320, 330, 340, 345, 346 are supplied and made available to a sensor measuring unit 300 suitable for this purpose and associated with the calculation and control unit 200. The sensor measuring unit 300 may be an independent measuring module or a sub-module of the calculation and control unit 200 (FIG. 4). In an optional embodiment, the moisture sensor 320 may include a reference temperature sensor 340. The calculation and control unit 200 may be configured to standardize the measured value of the moisture sensor 320 using the reference temperature sensor 340. The calculation and control unit 200 may determine the absolute from the relative humidity using knowledge of ambient and gas temperatures, pressure levels, and thus convert the ambient conditions of the sample gas that are current at the time of measurement into standardized conditions accordingly for the corrections required in determining the gas concentration of the further gas and in determining the oxygen concentration. As standardized conditions can be mentioned for example:

ATPS (Ambient Temperature Pressure Saturated), 20° C., 1013 hPa, saturated with moisture, BTPS (Body Temperature Pressure Saturated), 37° C., 1013 hPa, saturated with moisture, STPD (Standard Temperature Pressure Dry), 0° C., 1013 hPa, without moisture in the gas mixture.

With the gas guide 398, measuring gas in the measuring device 1 can reach the measuring chamber 380 via a gas supply 385. In the measuring chamber 380, the measuring gas flows around the measuring element 2 and the temperature sensor 330 and exits again via a gas outlet 395. In the area of the gas outlet 395, the first thermistor (NTC) 345, the second thermistor (NTC) 346, the pressure sensor 310, and the moisture sensor 320 with the optional reference temperature sensor 340 are arranged in a purge chamber 390. The second thermistor (NTC) is located in the gas outlet 395 in the flow shadow of a shadow element 347. The calculation and control unit 200 is configured to determine, on the basis of the measured values of the first thermistor 345 and the second thermistor 346, whether a flow 398 is present in the gas outlet 395 and to provide an output signal 268 which indicates a flow situation in the purge chamber 390—and thus indirectly also in the measurement chamber 380, in the gas outlet 395, and in the gas supply 385. The output signal 268 may be used, for example, to cause an indication relating to the flow situation to be provided on the output unit 220 or to be provided to a data network 900.

Figure 7:
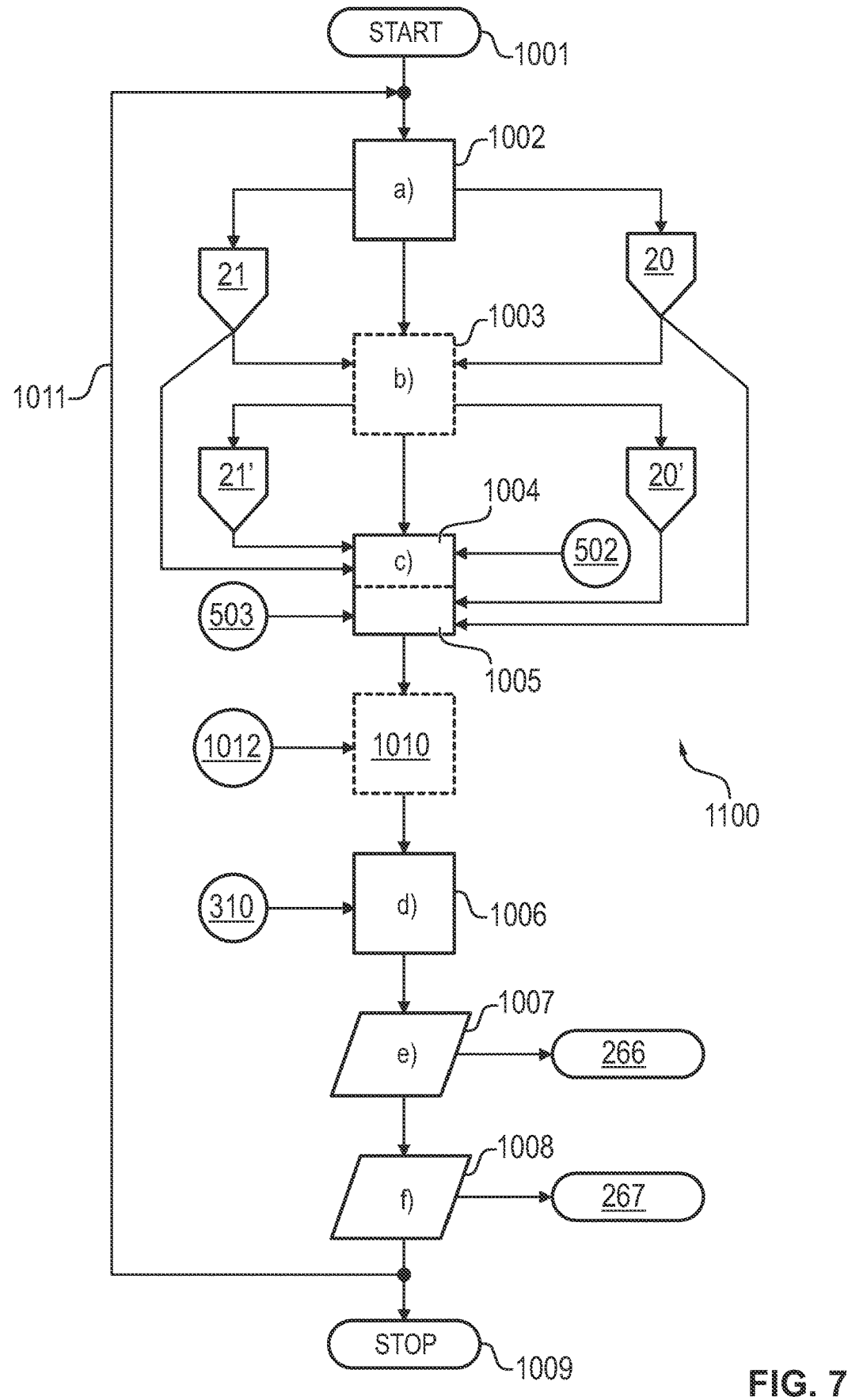
FIG. 7 is a flow diagram showing an exemplary procedure for operating the measuring system.

FIG. 7 shows an exemplary sequence 1100 of the process for operating the measuring system 100 (FIG. 4) for a determination of gas concentrations in a gas mixture of a gas sample in a flow chart with an exemplary step sequence of several steps. FIG. 7 is to be read in addition to, or in conjunction with, the figure description for FIG. 4. Identical elements in FIGS. 1, 2, 3a, 3b, 3c, 3d, 3f, 3g 3h, 3i, 4, 5, 6 and in FIG. 7 are designated by the same reference numerals in FIGS. 1, 2, 3a, 3b, 3c, 3d, 3f, 3g 3h, 3i, 4, 5, 6 and FIG. 7. The sequence 1100 of steps of a basic process for operating the measuring system 100 (FIG. 4) comprising steps 1001, 1002, 1003, 1004, 1005, 1006, 1007, 1008 and 1009 comprises the following process steps after a start 1001 to an end 1009:

a. Signal separation 1002 with division of the thermoelectric voltage signals into a direct voltage signal component (DC component) 20 and an alternating voltage signal component 21.

b. Optional moisture compensation 1003 of the AC voltage signal components 21 and/or optional moisture compensation of the DC voltage signal components 20. Optional signals are then AC voltage signal components 21' and/or DC voltage signal components 20' compensated for moisture.

c. Standardization 1004 of the AC voltage signal components 21, or the moisture compensated AC voltage signal components 21' to a reference signal 502. This results in standardized AC voltage signal components $U_{Y\sim}$.

Standardization 1005 of the DC voltage signal components 20, or of the moisture-compensated DC voltage signal components 20' to a reference signal 503. This results in standardized DC voltage signal components $U_{Y=}$.

d. Pressure compensation 1006 of the AC signal components 21 using information indicative of the current pressure level 310 in the gas mixture of the gas sample.

e. Calculating 1007 the oxygen concentration and providing an output signal 266 indicative of the oxygen concentration in the gas mixture of the gas concentration.

f. calculating 1008 the concentration of the further gas and providing an output signal 267 indicating the concentration of the further gas, in particular the anesthetic gas concentration, in the gas mixture.

After calculation and output of oxygen concentration and concentration of the further gas, a return 1011 is performed to the start 1001 and the sequence 1100 and is performed continuously. In a further optional step 1010, in this exemplary sequence 1100 according to this FIG. 7, an adjustment of the heat conductive and heat dissipative properties 1012 of the measuring element can be performed.

In the further optional step 1010, in the exemplary sequence 1100 of this FIG. 7, a pressure compensation of the DC signal components 20 can take place.

In this FIG. 7, the optional moisture compensation 1003 is also made clear pictorially by dashed line form in the steps 1003, 1004, 1005, so that according to the FIG. 7 it is to be represented in the sequence 1100 that, for example, also no moisture compensation must take place, in such a case a standardization of the alternating voltage signal components 21 to the reference signal 502 takes place in the step 1004 and a standardization of the direct voltage signal components 20 to the reference signal 503 takes place in the step 1005. However, FIG. 7 also depicts the following further options for steps 1004, 1005 with:

Step 1004: Standardization of the AC voltage signal components 21 to the reference signal 502, Step 1005: Standardization of the moisture compensated DC signal components 20' to the reference signal 503.

Step 1004: standardization of the moisture compensated AC signal components 21' to the reference signal 502, Step 1005: Standardization of the moisture compensated DC voltage signal components 20' to the reference signal 503.

Step 1004: standardization of the moisture compensated AC signal components 21' to the reference signal 502, Step 1005: standardization of the DC signal components 20 to the reference signal 503.

In all cases, the steps 1004, 1005 are followed by a pressure compensation 1006 of the AC voltage signal components 21. In an optional embodiment of the sequence 1100, a pressure compensation of the DC voltage signal components 20 can also be performed, for example in the further optional step 1010.

While specific embodiments of the invention have been shown and described in detail to illustrate the application of the principles of the invention, it will be understood that the invention may be embodied otherwise without departing from such principles.

LIST OF REFERENCE NUMBERS

1 Measuring device
2 Measuring element
3 Air gap
4 Electromagnet
5 Coil
6 Heat conduction measuring unit
7 Membrane
8 Heating structure
9 Measuring point
Amplifier
11 Voltage divider
12 DC voltage source
13 Low Pass Arrangements, Low Pass Filter, Low Pass
14 High Pass Arrangements, High Pass Filter, High Pass
15 Shunt
16 Multiplier
17 inverting amplifier
20, 20' DC voltage signal component (thermal conduction signal) $U_{X\sim}$, $U_{XF=}$
21, 21' AC voltage signal component (oxygen signal) $U_{X=}$, $U_{XF\sim}$
22 Heating capacity
23 Heating current
24 Heating voltage
25 Modulation-related signals (oxygen)
100 Measuring system
101-109 Circuit arrangements
200 Calculation and control unit
201, 202 Diagrams
203 Records, association, table, data field (array)
204 Magnetic field control
205 Signal processing
206 Data interface
207 Data memory, calculation module, µC, RAM, ROM
220 Output unit
244 Control lines to the solenoid
255 Signal lines from measuring element
266, 267 Output signals
300 Sensor measuring unit
310 Pressure sensor, pressure reading, pressure measurement signal information or data on the pressure level in the gas sample
320 Moisture sensor, moisture measured value, moisture measurement signal Information or data on moisture in the gas sample
330 Temperature sensor, temperature measured value, temperature measurement signal information or data on the temperature in the gas sample
340 Reference temperature sensor
345, 346 Thermistors (NTC's)
347 Shadow element
380 Measuring chamber
385 Gas supply
390 Purge chamber
395 Gas outlet
398 Gas guide
399 Ordinate (x-axis)
400, 450 Scaling values, reference values, standardization values 499 Abscissa (y-axis)
500, 600, 700, 800 Gas compositions (dry), gas samples
501, 601, 701, 801 Thermoelectric voltage signals of dry gas compositions
502, 602, 702, 802 Thermo-voltage signals (AC voltage signal component)
503, 603, 703, 803 Thermo-voltage signals (DC signal component)
502, 503 Reference values for standardization
505, 605, 705, 805 Thermoelectric voltage signals of the humid gas mixtures
506, 606, 706, 806 Thermo voltage signals (AC voltage signal component)
507, 607, 707, 807 Thermo-voltage signals (DC signal component)
508, 608, 708, 808 Gas compositions (wet)
900 Data network
1000 Demarcation line
1001-1011 Step sequence for operating the measuring system
1012 heat conducting/heat dissipating properties of the measuring element
1100 Flowchart

What is claimed is:

1. A measuring system for determining gas concentrations in a gas mixture, the measuring system comprising: a measuring device comprising: a measuring element in a measuring chamber; an electromagnet; and a coil, wherein the measuring element includes a membrane with a heating structure; a gas supply configured to supply a quantity of a gas mixture of a gas sample to the measuring element; a gas outlet; a circuit arrangement cooperating with the measuring device to heat the heating structure on the membrane of the measuring element and cooperating with the electromagnet and the coil of the measuring device to generate a magnetic field acting on the measuring element, wherein the circuit arrangement is configured to operate the measuring device with the measuring element and the electromagnet and the coil and is configured to provide measured values with an alternating voltage signal component and with a DC signal component to a calculation and control unit; the calculation and control unit configured to consider or compensate for environmental conditions and configured to provide a standardization of the AC voltage signal component and a standardization of the DC voltage signal component to a reference value to provide standardized AC voltage signal components and standardized DC signal components, is configured to determine an oxygen concentration in the gas mixture of the gas sample based on the standardized alternating voltage signal components, configured to determine a concentration of another gas in the gas mixture of the gas sample based on the standardized DC voltage signal components and is configured to generate output signals, which indicate the determined oxygen concentration and the determined concentration of another gas in the gas mixture of the gas sample.

2. The measuring system according to claim 1, wherein the calculation and control unit is configured to determine the oxygen concentration, or determine the concentration of the further gas in the gas mixture of the gas sample, or both determine the oxygen concentration and determine the concentration of the further gas in the gas mixture of the gas sample based further on data sets previously determined in measurements, which represent a correlation of signal curves to concentrations of the further gas and oxygen in the gas mixture of the gas sample.

3. The measuring system according to claim 2, wherein the data sets are stored in the form of a data field or several data fields or are stored in the form of a function or assignment rule.

4. The measuring system according to claim 1, wherein the calculation and control unit is configured to determine the oxygen concentration, or determine the concentration of the further gas in the gas mixture of the gas sample, or both determine the oxygen concentration and determine the concentration of the further gas in the gas mixture of the gas sample based further on a measured value of a pressure sensor, which indicates a pressure level of the gas mixture of the gas sample, or based further on provided pressure level information with regard to a pressure level of the gas mixture of the gas sample or based further on both a measured value of a pressure sensor, which indicates a pressure level of the gas mixture of the gas sample, and provided pressure level information with regard to a pressure level of the gas mixture of the gas sample.

5. The measuring system according to claim 4, wherein a sensor measuring unit is provided and is associated with the calculation and control unit to detect at least one of measured values of a moisture sensor and is configured to provide acquired measured values or data derived from measured values of the moisture sensor to the calculation and control unit.

6. The measuring system according to claim 1, wherein the measuring device or the calculation and control unit or both the measuring device and the calculation and control unit are configured to heat the measuring chamber or the gas supply or both the measuring chamber and the gas supply.

7. The measuring system according to claim 1, wherein the calculation and control unit is configured to determine the oxygen concentration, or determine the concentration of the further gas in the gas mixture of the gas sample, or both determine the oxygen concentration and determine the concentration of the further gas in the gas mixture of the gas sample based further on a measured value of a moisture sensor, which indicates a moisture in the gas mixture of the gas sample or based further on provided information with regard to moisture in the gas mixture of the gas sample, or based further on a measured value of a temperature sensor, which indicates a temperature of the gas mixture of the gas sample, or based further on provided information regarding a temperature of the gas mixture of the gas sample or based further on any combination of a measured value of a moisture sensor, which indicates a moisture in the gas mixture of the gas sample, and provided information with regard to moisture in the gas mixture of the gas sample and a measured value of a temperature sensor, which indicates a temperature of the gas mixture of the gas sample, and provided information regarding a temperature of the gas mixture of the gas sample.

8. The measuring system according to claim 7, wherein the moisture sensor is arranged in a purge chamber of the measuring device.

9. The measuring system according to claim 8, wherein the purge chamber is arranged in a gas flow and in the measuring device at the measuring element or in relation to the measuring element and in relation to the gas flow such that the flowing gas mixture of the gas sample flows into and through the purge chamber after flowing around or over a surface of the membrane of the measuring element.

10. The measuring system according to claim 8, wherein: at least one resistance measuring element is arranged in the purge chamber in a gas flow and another resistance measuring element is arranged behind a shadow element; and the calculation and control unit is configured to determine a flow condition based on the measured values of at least one resistance measuring element or both resistance measuring elements.

11. The measurement system according to claim 10, wherein the calculation and control unit is configured to determine, based on the data from the resistance measurement elements, whether a condition is present with a flow through the purge chamber with the gas mixture of the gas sample.

12. The measuring system according to claim 11, wherein the calculation and control unit is configured to determine the oxygen concentration, or determine the concentration of the further gas in the gas mixture of the gas sample, or both determine the oxygen concentration and determine the concentration of the further gas in the gas mixture of the gas sample based on provided information regarding a gas composition of the gas mixture of the gas sample.

13. The measuring system according to claim 7, wherein: the moisture sensor comprises a reference temperature sensor; and the calculation and control unit is configured to standardize the measured value of the moisture sensor using the reference temperature sensor.

14. The measuring system according to claim 1, wherein the calculation and control unit is configured to determine the oxygen concentration, or determine the concentration of the further gas in the gas mixture of the gas sample, or both determine the oxygen concentration and determine the concentration of the further gas in the gas mixture of the gas sample based further on information provided regarding a dosing state of a dosing system, information provided in relation to respiratory phases, or information provided regarding operating conditions of an anesthesia device or ventilator.

15. The measuring system according to claim 1, wherein: the measuring system is supplied with a gas sample of a gas mixture by a gas supply; the gas sample is: an expiratory gas sample from an expiratory feed line, an inspiratory gas sample from an inspiratory feed line, or a patient gas sample from a patient connecting element or an internal gas sample from a sampling point of the gas line; and the calculation and control unit is configured to determine gas concentrations of oxygen and of a further gas in the gas samples.

16. A process for determining gas concentrations in a gas mixture of a gas sample using measured values with an alternating voltage signal component and with a direct voltage signal component, the process comprising the steps of: separating thermo-voltage signals into a DC voltage signal component and an AC voltage signal component; standardizing the AC voltage signal components and the DC voltage signal components to reference values in order to obtain standardized AC voltage signal components and standardized DC voltage signal components; pressure compensating the standardized alternating voltage signal components based on measured values of a pressure sensor or information indicating current pressure level in the gas mixture of the gas sample; determining an oxygen concentration in the gas mixture of the gas sample based on the AC signal components; determining an anesthetic gas concentration in the gas mixture of the gas sample based on the DC signal components; and providing an output signal, which indicates a concentration of a further gas and the oxygen concentration in the gas mixture of the gas sample.

17. The process according to claim 16, wherein in one of the steps or in a further step a moisture compensation of the AC signal components and/or DC signal components is performed by including measured values of a moisture sensor or information indicating a moisture content in the gas mixture of the gas sample.

18. The process according to claim 16, wherein in one of the steps or in a further step, a matching of heat-conducting and heat-dissipating properties of a measuring element is carried out.

19. The process according to claim 16, wherein in a further step a pressure compensation of the DC signal components or of the standardized DC signal components is performed by including measured values of a pressure sensor or information indicating a current pressure level of the gas mixture of the gas sample.

20. The process according to claim 16, wherein in a further step moisture and/or temperature compensation of the AC voltage signal components or of the standardized AC voltage signal components and/or of the DC voltage signal components or of the standardized DC voltage signal components is carried out.

* * * * *